US012758335B2

(12) United States Patent
Gonzalez Chapa et al.

(10) Patent No.: US 12,758,335 B2
(45) Date of Patent: Oct. 13, 2026

(54) ROBOTIC SYSTEMS WITH VIBRATION COMPENSATION, AND RELATED METHODS

(71) Applicant: Monogram Technologies Inc., Austin, TX (US)

(72) Inventors: Gerardo Angel Gonzalez Chapa, Austin, TX (US); Scott Hudson, Pflugerville, TX (US)

(73) Assignee: Monogram Technologies, Inc., Austin, TX (US)

( * ) Notice: Subject to any disclaimer, the term of this patent is extended or adjusted under 35 U.S.C. 154(b) by 48 days.

(21) Appl. No.: 18/773,996

(22) Filed: Jul. 16, 2024

(65) Prior Publication Data

US 2024/0366325 A1 Nov. 7, 2024

Related U.S. Application Data

(63) Continuation of application No. PCT/US2023/061119, filed on Jan. 23, 2023.

(Continued)

(51) Int. Cl.

*A61B 34/32* (2016.01)
*A61B 17/16* (2006.01)

(Continued)

(52) U.S. Cl.

CPC .............. *A61B 34/32* (2016.02); *A61B 17/16* (2013.01); *A61B 34/75* (2016.02); *A61B 2034/305* (2016.02)

(58) Field of Classification Search

CPC ......... A61B 34/30; A61B 34/32; A61B 34/37; A61B 17/16; A61B 17/142;

(Continued)

(56) References Cited

U.S. PATENT DOCUMENTS 10,682,141 B2 * 6/2020 Moore ............... A61B 17/0686
2012/0116391 A1 * 5/2012 Houser .................. A61B 34/76 606/1

(Continued)

FOREIGN PATENT DOCUMENTS

AU 2023209896 9/2024
AU 2023209942 9/2024

(Continued)

OTHER PUBLICATIONS

International Search Report and Written Opinion of the International Search Authority, International Application No. PCT/US2023/061119, 12 pages, dated Jul. 3, 2023.

(Continued)

*Primary Examiner* — Shaun L David
*Assistant Examiner* — Cherie M Poland
(74) *Attorney, Agent, or Firm* — SCHWEGMAN LUNDBERG & WOESSNER, P.A.

(57) ABSTRACT

Robotic to mitigate and withstand vibration forces including an articulated arm comprising a plurality of arm segments, and adjustable joints coupled between adjacent arm segments. The robotic systems include an end effector rotatably coupled to an end arm segment comprising a powered drive portion. The end effector comprises a cutting tool attachment mechanism that is configured to couple with a cutting tool such that the cutting tool extends axially therefrom, and the powered drive portion translates the cutting tool along a cutting pathway along which the cutting tool is configured to effectuate cutting that is angled with respect to a longitudinal axis of the cutting tool. The end effector is oriented such that the longitudinal axis of the cutting tool, and that of the end effector itself, are angled with respect to the longitudinal axis of the end arm segment.

35 Claims, 13 Drawing Sheets

Related U.S. Application Data

(60) Provisional application No. 63/302,122, filed on Jan. 23, 2022.

(51) Int. Cl.
*A61B 34/00* (2016.01)
*A61B 34/30* (2016.01)

(58) Field of Classification Search
CPC ..... A61B 2017/00477; A61B 2034/305; B25J 11/005; B25J 15/04
See application file for complete search history.

(56) References Cited

U.S. PATENT DOCUMENTS

| | | | | |
|---|---|---|---|---|
| 2017/0252113 | A1 | 9/2017 | Beelen et al. | |
| 2017/0348007 | A1* | 12/2017 | Shiels | A61B 17/142 |
| 2018/0008270 | A1* | 1/2018 | Moore | A61B 50/20 |
| 2018/0168750 | A1 | 6/2018 | Staunton et al. | |
| 2018/0228501 | A1 | 8/2018 | Shen et al. | |
| 2018/0353253 | A1 | 12/2018 | Bowling | |
| 2020/0022761 | A1 | 1/2020 | Cone et al. | |
| 2020/0030046 | A1 | 1/2020 | Bowling | |
| 2020/0323540 | A1 | 10/2020 | Kang et al. | |
| 2021/0093333 | A1* | 4/2021 | Chappuis | A61B 34/30 |
| 2024/0423736 | A1 | 12/2024 | Shamaei et al. | |
| 2025/0339977 | A1 | 11/2025 | Gonzalez Chapa | |

FOREIGN PATENT DOCUMENTS

| | | |
|---|---|---|
| CA | 3249314 | 7/2023 |
| CA | 3249317 | 7/2023 |
| EP | 3409231 | 12/2018 |
| EP | 4465916 | 11/2024 |
| EP | 4468989 | 12/2024 |
| JP | 2025504507 | 2/2025 |
| JP | 2025504886 | 2/2025 |
| KR | 20240165931 | 11/2024 |
| KR | 20240168303 | 11/2024 |
| WO | 2017075548 | 5/2017 |
| WO | 2017158263 | 9/2017 |
| WO | 2018081905 | 5/2018 |
| WO | 2018103945 | 6/2018 |
| WO | 2019055904 | 3/2019 |
| WO | 2020236937 | 11/2020 |
| WO | 2021064331 | 4/2021 |
| WO | 2021140513 | 7/2021 |
| WO | 2021231373 | 11/2021 |
| WO | 2022001320 | 1/2022 |
| WO | 2023141644 | 7/2023 |
| WO | 2023141663 | 7/2023 |

OTHER PUBLICATIONS

"European Application Serial No. 23744026.8, Extended European Search Report mailed Dec. 15, 2025", 11 pgs.
"European Application Serial No. 23744008.6, Extended European Search Report mailed Jan. 2, 2026", 8 pgs.
"European Application Serial No. 23744008.6, Response to Communication pursuant to Rules 161(2) and 162 EPC filed Mar. 3, 2025", 11 pgs.
"International Application Serial No. PCT US2023 061119, International Search Report mailed Jul. 3, 2023", 2 pgs.
"International Application Serial No. PCT US2023 061119, Written Opinion mailed Jul. 3, 2023", 9 pgs.
"International Application Serial No. PCT US2023 061119, Invitation to Pay Additional Fees mailed Feb. 14, 2023", 4 pgs.
"International Application Serial No. PCT US2023 061119, International Preliminary Report on Patentability mailed Aug. 2, 2024", 11 pgs.
"European Application Serial No. 23744026.8, Response to Communication pursuant to Rules 161(2) and 162 EPC filed Mar. 3, 2025", 16 pgs.
"International Application Serial No. PCT US2023 061201, International Search Report mailed Jun. 8, 2023", 3 pgs.
"International Application Serial No. PCT US2023 061201, Written Opinion mailed Jun. 8, 2023", 10 pgs.
"International Application Serial No. PCT US2023 061201, International Preliminary Report on Patentability mailed Aug. 8, 2024", 12 pgs.

* cited by examiner

ROBOTIC SYSTEMS WITH VIBRATION COMPENSATION, AND RELATED METHODS

CROSS-REFERENCE TO RELATED APPLICATIONS

The present application is a bypass continuation of International Application No. PCT/US2023/061119, entitled Robotic Systems with Vibration Compensation, and Related Methods, filed on Jan. 23, 2023, which perfects and claims priority benefit of U.S. Provisional Application No. 63/302,122, entitled Robotic Systems with Vibration Compensation, and Related Methods, filed on Jan. 23, 2022, the entireties of which are hereby expressly incorporated herein by reference.

FIELD OF THE DISCLOSURE

The following disclosure relates generally to improved surgical robots, components thereof and related systems. More particularly, the following disclosure relates to surgical robotic systems, components thereof and related systems that minimize the effects of vibration from an end effector on a cutting tool to ensure precise bone and tissue cutting.

BACKGROUND

Powered cutting tools, such as oscillating saws and rotary burrs, have been used to reduce operating time and surgeon labor, and improve accuracy, in orthopedic surgical procedures. Such powered cutting tools enable faster and more accurate cutting of bone and other tissue during surgical procedures as compared to fully manual cutting tools, for example.

Recently, surgical robots have become available which can control the power cutting tools used in orthopedic surgical procedures so as to provide superior accuracy in cutting bone. Surgical robots include a robotic arm, which is typically articulated, that either provides or facilitates the gross movement of the cutting tool, such as along cutting pathways. Some current surgical robots are configured as hand-guided instruments that power the cutting tool and assist a user in translating the cutting tool to (and through) the patient, but require a user to manually move and direct the cutting tool along its cutting pathway (i.e., the robot is not actively executing the cuts). For example, some such surgical robots include a handle and a trigger that a user manually utilizes to move and direct an active cutting tool along its cutting pathway.

With orthopedic surgical robots, a key factor in determining the safety, accuracy and efficiency of the cutting performed by the robot is control of the toolpath. However, typical surgical robots include a power module or end effector that powers the cutting blade such that the cutting blade is translating along a cutting direction defined by the cutting edge(s) thereof along which the cutting blade is designed to cut. The cutting blade motion effectuated by an end effector necessarily induces vibration into the robotic arm, which thereby prevents total control of the toolpath. For example, vibration from instruments that are mounted on the robotic arm can affect the performance of components of the robot, and can adversely impact the overall cutting performance of the robot during a cutting operation, and thereby cause the cutting tool to move outside an intended cut path. The vibrations created by an end effector and cutting blade, inter alia, can also cause damage the robotic arm. For example, vibration passing through a surgical robot can cause damage one or more components of the robot, such as a due to wear and/or an acute failure.

The present disclosure provides improved surgical robots, robotic system components, and related surgical methods, that inhibit the generation of destructive vibratory forces/motions and/or mitigate vibratory forces/motions, to enhance the safety, accuracy and efficiency of surgical cutting. The present disclosure provides also improved surgical robots, robotic system components, and related surgical methods, that inhibit the generation of destructive vibratory forces/motions and/or mitigate vibratory forces/motions, to prevent failure of the components of the robot. As the surgical robots, robotic system components, and related surgical methods of the present disclosure provide for safe, accurate and reliable cutting of tissue (e.g., bone and/or soft tissue), fully autonomous surgical and related surgical methods can thereby also be provided.

While certain aspects of conventional technologies have been discussed to facilitate disclosure of Applicant's inventions, the Applicant in no way disclaims these technical aspects, and it is contemplated that the inventions may encompass one or more conventional technical aspects.

In this disclosure, where a document, act or item of knowledge is referred to or discussed, this reference or discussion is not an admission that the document, act or item of knowledge or any combination thereof was, at the priority date, publicly available, known to the public, part of common general knowledge, or otherwise constitutes prior art under the applicable statutory provisions; or is known to be relevant to an attempt to solve any problem with which this specification is concerned.

SUMMARY

The present inventions may address one or more of the problems and deficiencies of current surgical robots, surgical robot system components and related surgical methods. However, it is contemplated that the inventions may prove useful in addressing other problems and deficiencies in a number of technical areas. Therefore, the claimed invention(s) should not necessarily be construed as limited to addressing any of the particular problems or deficiencies discussed herein.

The present disclosure is generally directed to surgical robots, surgical robot system components and related surgical methods. The present disclosure provides surgical robotic arms that include a power module or end effector that powers a cutting blade and are configured to prevent and/or mitigate the generation of vibrations that pass through the arm and the components thereof. The present disclosure also provides such powered surgical robotic arms that are configured to prevent and/or mitigate the likelihood that any vibrations that are generated are adequately controlled by the robot such that the robot maintains control of the toolpath along an intended cut path. The present disclosure also provides such powered surgical robotic arms that include components that are configured to prevent and/or mitigate the likelihood of damage and/or failure thereof via vibrations that are generated. The vibration prevention and mitigation features of the surgical robots, robotic system components, and related surgical methods of the present disclosure provide for safe, accurate and reliable cutting of tissue (e.g., bone and/or soft tissue). Still further, due to the vibration prevention and mitigation features, fully autonomous surgical and related surgical methods are also provided for herein. In fully autonomous embodiments wherein the surgical robot autonomously executes pre-determined surgical cuts (via following pre-planned cut paths), the robots and methods allow a user (e.g., a surgeon) to perform other surgical tasks (e.g., tasks that utilize one or both of the user's hands) during the cutting operations, and allows for open working space in an operating room.

In some embodiments, the vibration prevention and mitigation features of the surgical robots, robotic system components, and related surgical methods of the present disclosure comprise vibration prevention/mitigation instrument design, vibration prevention/mitigation instrument mounts, vibration prevention/mitigation instrument operation (such as, but not limited to, vibration prevention/mitigation optimizations of tool motion) (e.g., harmonic vibration), and vibration prevention/mitigation add-on components (such as, but not limited to, tuned mass dampers) The vibration prevention and mitigation features may be utilized individually, or a combination (e.g., all) of the vibration prevention and mitigation features may be utilized, in a surgical robot (or robotic system) or related surgical method.

It is noted that the cutting tool may be any cutting tool, such as but not limited to a surgical cutting tool configured to cut or resect tissue. In one exemplary embodiment, the cutting tool is a cutting blade or saw (e.g., a sagittal surgical saw blade). Similarly, the end effector may be any instrument configured to move (e.g., reciprocate or rotate) the cutting tool along a direction that the cutting edge is configured to cut (e.g., in a direction extending along the cutting edge), such as a powered sagittal saw end effector. The end effector may be coupled between a distal arm segment of the robotic arm and the cutting tool, and its configuration may be optimized to minimize the production of vibrations during operation of the cutting tool within its predefined operating parameters, and/or mitigate the strength and/or application of the vibrations on aspects or components of the robotic system.

In one aspect, the present disclosure provides a robotic system comprising an articulated arm comprising a plurality of arm segments defining longitudinal axes, and adjustable joints coupled between adjacent arm segments that are configured to adjust the orientation of the axes of the adjacent arm segments; and an end effector rotatably coupled to an arm end segment of the plurality of arm segments comprising a powered drive portion. The end effector comprises a cutting tool attachment mechanism positioned at a longitudinal end of the end effector that is configured to couple with a cutting tool such that the cutting tool extends axially therefrom, and the drive portion translates the cutting tool along a cutting pathway along which the cutting tool is configured to effectuate cutting that is angled with respect to a longitudinal axis of the cutting tool. The end effector is oriented such that the longitudinal axis of the cutting tool is angled with respect to the axis of the end arm segment.

In some embodiments, the cutting tool is configured to cut when oscillated along the cutting pathway about an axis of oscillation. In some embodiments, the wherein the end effector is oriented such that the longitudinal axis of the cutting tool is angled with respect to the axis of the end arm segment. In some embodiments, the end effector is oriented such that the longitudinal axis of the cutting tool is oriented substantially perpendicular with respect to the axis of the end arm segment. In some embodiments, the end effector defines a second longitudinal axis, and wherein the end effected is oriented such that the second longitudinal axis is angled with respect to the axis of the end arm segment. In some embodiments, the second longitudinal axis is oriented substantially perpendicular with respect to the axis of the end arm segment.

In some embodiments, the end effector is longitudinally elongated such that is defines a maximum longitudinal length that is greater than a maximum lateral width. In some embodiments, the end arm segment is rotatable coupled with a lateral side portion of the end effector that is longitudinally spaced from a longitudinally end of the end effector that opposes the attachment mechanism. In some embodiments, the cutting tool is configured as a sagittal cutting tool with cutting teeth positioned at the longitudinal end thereof, the sagittal cutting tool being configured to cut when oscillated along the cutting pathway about the axis of oscillation and translated longitudinally.

In some embodiments, the cutting tool is configured such that it comprises a center of mass that is substantially aligned with the axis of oscillation. In some embodiments, the cutting tool is configured such that the axis of oscillation is substantially aligned with the longitudinal axis thereof.

In some embodiments, the attachment mechanism comprises an attachment arm with a first portion that is coupled with the drive portion and extends longitudinally therefrom, wherein the attachment arm is oscillated by the drive portion about a second axis of oscillation, and wherein the attachment arm is configured to transfer said oscillation to the cutting tool to oscillate the cutting tool. In some embodiments, the attachment arm is configured such that the second axis of oscillation is substantially aligned with a longitudinal axis thereof. In some embodiments, the attachment arm is configured such that it comprises a center of mass that is substantially aligned with the second axis of oscillation. In some embodiments, the first and second axes of oscillation are parallel.

In some embodiments, the cutting tool comprises a cutting tool with a body portion that comprises plurality of longitudinally spaced apertures to minimize the total mass of the cutting tool. In some embodiments, the preceding claims, wherein the attachment arm comprises a body portion comprises at least aperture to minimize the total mass of the attachment arm. In some embodiments, the drive portion of the end effector is configured to apply an oscillatory force at a frequency that greater than or less than a resonant frequency range of the robotic system and that oscillates the cutting tool along the cutting pathway in a cutting operation frequency range of the cutting tool.

In some embodiments, the end effector is coupled to the end arm segment such that the end effect is rotatable about the axis of the end arm segment. In some embodiments, the end effector is coupled to the end arm segment such that the end effect is only rotatable about the axis of the end arm segment.

In some embodiments, the end effector is coupled to the end arm segment via a rotatable joint. In some embodiments, the rotatable joint comprises a flange assembly with a first connector coupled to the end effector and a flange connector assembly coupled to the end arm segment, wherein the flange connector comprises a projection that extends into a recess in the end effector. In some embodiments, the rotatable joint further comprises a flexible vibration dampening member positioned within the recess between the recess and the projection. In some embodiments, the rotatable joint further comprises a flexible vibration dampening member positioned within the recess between the recess and the projection. In some embodiments, the vibration dampening member is under a compressive preload.

In some embodiments, the cutting tool comprises a cutting blade. In some embodiments, the robotic system is configured as an autonomous robot that autonomously translates the cutting tool through one or more cutting pathways without a user physically engaging the robotic system.

In another aspect, the present disclosure provides a method of cutting a material comprising utilizing a robotic system as described above to translate the cutting tool along the cutting pathway and one or more longitudinal pathways to cut the material.

In some embodiments, the material comprises a bone of a mammalian patient, and wherein the cutting tool comprises a sagittal cutting blade.

It should be appreciated that all combinations of the foregoing aspects and additional concepts discussed in greater detail below (provided such concepts are not mutually inconsistent) are contemplated as being part of the inventive subject matter and to achieve the advantages disclosed herein.

These and other objects, features and advantages of this disclosure will become apparent from the following detailed description of the various aspects of the disclosure taken in conjunction with the accompanying drawings.

BRIEF DESCRIPTION OF THE DRAWINGS

These and other features, aspects, and advantages of the present disclosure will become better understood when the following detailed description is read with reference to the accompanying drawings, which are not necessarily drawn to scale and in which like reference numerals represent like aspects throughout the drawings, wherein.

DETAILED DESCRIPTION

Figure 1:
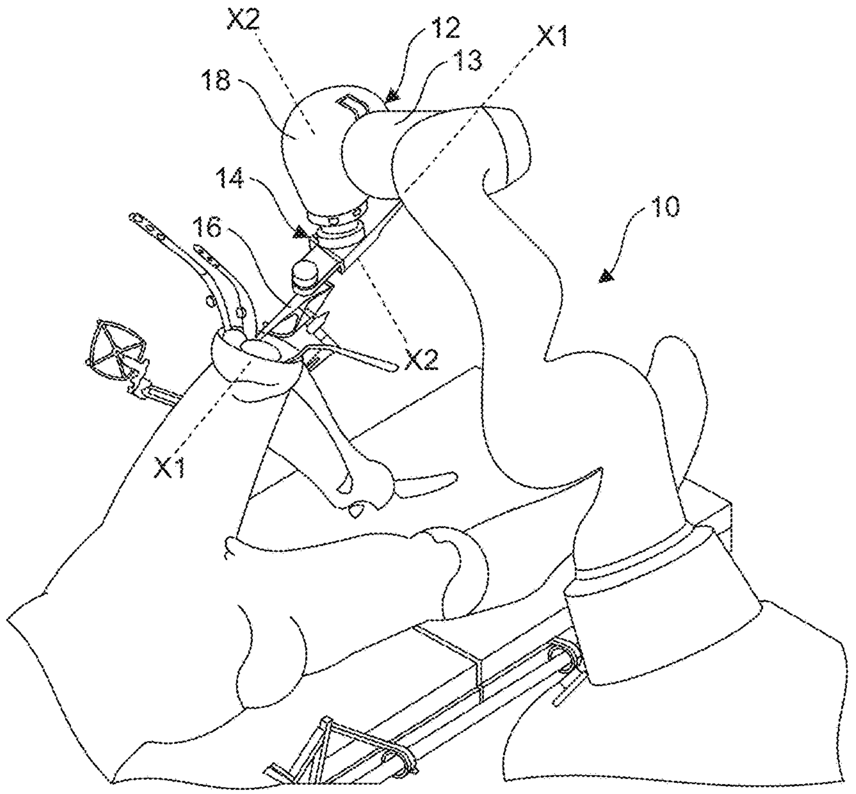
FIG. 1 illustrates, in one example, a surgical robot, in accordance with one or more aspects of the present disclosure.

Aspects of the present disclosure and certain examples, features, advantages, and details thereof, are explained more fully below with reference to the non-limiting examples illustrated in the accompanying drawings. Descriptions of well-known materials, fabrication tools, processing techniques, etc., are omitted so as not to unnecessarily obscure the relevant details. It should be understood, however, that the detailed description and the specific examples, while indicating aspects of the disclosure, are given by way of illustration only, and are not by way of limitation. Various substitutions, modifications, additions, and/or arrangements, within the spirit and/or scope of the underlying inventive concepts will be apparent to those skilled in the art from this disclosure.

Approximating language, as used herein throughout disclosure, may be applied to modify any quantitative representation that could permissibly vary without resulting in a change in the basic function to which it is related. Accordingly, a value modified by a term or terms, such as "about" or "substantially," is not limited to the precise value specified. For example, these terms can refer to less than or equal to ±5%, such as less than or equal to ±2%, such as less than or equal to #1%, such as less than or equal to ±0.5%, such as less than or equal to ±0.2%, such as less than or equal to ±0.1%, such as less than or equal to ±0.05%. In some instances, the approximating language may correspond to the precision of an instrument for measuring the value. Any examples of operating or configuration parameters are not exclusive of other parameters of the disclosed embodiments.

Terminology used herein is for the purpose of describing particular examples only and is not intended to be limiting. As used herein, the singular forms "a", "an" and "the" are intended to include the plural forms as well, unless the context clearly indicates otherwise. Furthermore, references to "one example" are not intended to be interpreted as excluding the existence of additional examples that also incorporate the recited features. Moreover, unless explicitly stated to the contrary, the terms "comprising" (and any form of "comprise," such as "comprises" and "comprising"), "have" (and any form of "have," such as "has" and "having"), "include" (and any form of "include," such as "includes" and "including"), and "contain" (and any form of "contain," such as "contains" and "containing") are used as open-ended linking verbs. As a result, any examples that "comprises," "has," "includes" or "contains" one or more step or element possesses such one or more step or element, but is not limited to possessing only such one or more step or element.

As used herein, the terms "may" and "may be" indicate a possibility of an occurrence within a set of circumstances; a possession of a specified property, characteristic or function; and/or qualify another verb by expressing one or more of an ability, capability, or possibility associated with the qualified verb. Accordingly, usage of "may" and "may be" indicates that a modified term is apparently appropriate, capable, or suitable for an indicated capacity, function, or usage, while taking into account that in some circumstances the modified term may sometimes not be appropriate, capable or suitable. For example, in some circumstances, an event or capacity can be expected, while in other circumstances the event or capacity cannot occur—this distinction is captured by the terms "may" and "may be."

The term "coupled" and like terms are used herein to refer to both direct and indirect connections. As used herein and unless otherwise indicated, the term "entirety" (and any other form of "entire") means at least a substantial portion, such as at least 95% or at least 99%. The term "entirety" (and any other form of "entire"), as used herein, is thereby not limited to 100%, unless otherwise indicated. As used herein, the term "layer"

Components, aspects, features, configurations, arrangements, uses and the like described, illustrated or otherwise disclosed herein with respect to any particular embodiment may similarly be applied to any other embodiment disclosed herein.

As shown in FIG. 1, a robot or robotic system 10 with, inter alia, an articulated robotic arm 12, an end effector 14 and a cutting tool or device 16 is disclosed. As depicted in FIG. 1, the robot may be configured as a surgical robot. For example, the surgical robot 10 may be biocompatible, and configured be sterilized to such a degree, as required in surgical settings. However, in other embodiments, the robot 10 may be configured as an industrial or other non-surgical robotic device or system. The term "surgical robot" as used herein in reference to the exemplary illustrative robot/robotic system embodiments shown in FIGS. 1-13 is not mean in a limiting sense, and any and all description herein directed to a "surgical robot" or the like equally applies to a generic robot/robotic system or an industrial or other non-surgical robot/robotic system.

As explained further below, the surgical robot 10 may be configured to mitigate the generation and/or deleterious effects of vibrations during operation thereof, and is thus able to control the cut path of the cutting tool 16 thereof with an accuracy and reliability that enables the robot 10 to act autonomously. In some other embodiments, the surgical robot 10 may be configured as a user-guided robot that requires a user to manually (to a degree) translate the cutting tool 16 along desired cut paths.

The robot 10 may be operably connected to a computer system (e.g., memory, processor, etc.) (not shown) that controls movement of the cutting tool 16, via movement of the articulated arm 12 for example, and potentially operation of the end effector 14. For example, in some embodiments, the robot 10 may comprise part of a robotic system that includes a control unit, and potentially a user interface (UI). The control unit may include at least one processing circuit, at least one input/output device, and at least one storage device or memory having at least one database or cutting instructions stored therein. The control unit may have a control algorithm or programming code for controlling the position of the cutting tool 16 (such as via the joint angle between segments of the articulated arm 12, for example). The control algorithm or programming code may be a default control algorithm or include inputs from, for example, the UI and/or another interface.

The articulated arm 12 may extend from a base (not shown) and include a plurality of rigid arm or body segments/parts, and a plurality of joints that connect adjacent segments (and a first or base segment to the base), as shown in FIG. 1. The plurality of joints may include, for example, four, five or six individual segments that are coupled together via three, four or five joints, respectively. In some other embodiments, the articulated arm 12 may include at least two segments and at least one joint coupling the at least two segments together, or more than six segments and more than five joints coupling the segments together.

Each arm segment of the articulated arm 12 may define an axial axis extending along its longitudinal length. The joints may be configured such that the arm segments can rotate about their axes and/or articulate angularly with respect to each other such that the axes of adjacent segments are angularly offset. In some embodiments, one or more of the joints may be configured to allow multiple degrees of freedom between adjacent arm segments (and, potentially, the base segment and the base). In some such embodiments, at least one of the joints may be configured to provide six degrees of freedom. The articulated arm 12 may further comprise motors, actuators or other adjustment devices that are configured to adjust the axial rotation and/or angular orientation between adjacent segments. In this way, the robot 10 can utilize the articulated arm 12 to translate the cutting tool 10 three-dimensionally in space and relative to a workpiece (e.g., a patient) to, ultimately, cut one or more portions of the workpiece. As noted above, the robot 10 may include control software that dictates or instructs, inter alai, the articulated arm 12 of the robot 10 to adjust in particular ways (i.e., adjustment of the joints) to accomplish prescribed movements of the cutting tool 16.

The base of the surgical robot 10 may be fixed to, for example, a movable cart or the ground, such that the base may provide a fixed frame of reference for defining the position, orientation, and motion of the plurality of joints and the plurality of arm segments relative to the base. The base may be used to define a frame of reference, such as, for example, a set of three-dimensional axes (e.g., x, y, z), which may be used to define positions, orientations, and motions of the surgical robot 10 and of objects relative to the surgical robot 10. A frame of reference defined relative to the base may also be known as a world frame, a base, a base frame, a frame, or a tool frame. It is noted that with the position and orientation of an object defined or calculated in relation to the fixed frame of reference, the object may also be defined in the same frame of reference as the surgical robot 10, and the surgical robot 10 may calculate the position and orientation of the object. As such, the surgical robot 10 may programmably interact with the defined objects, positions, and/or orientations.

Figure 2:
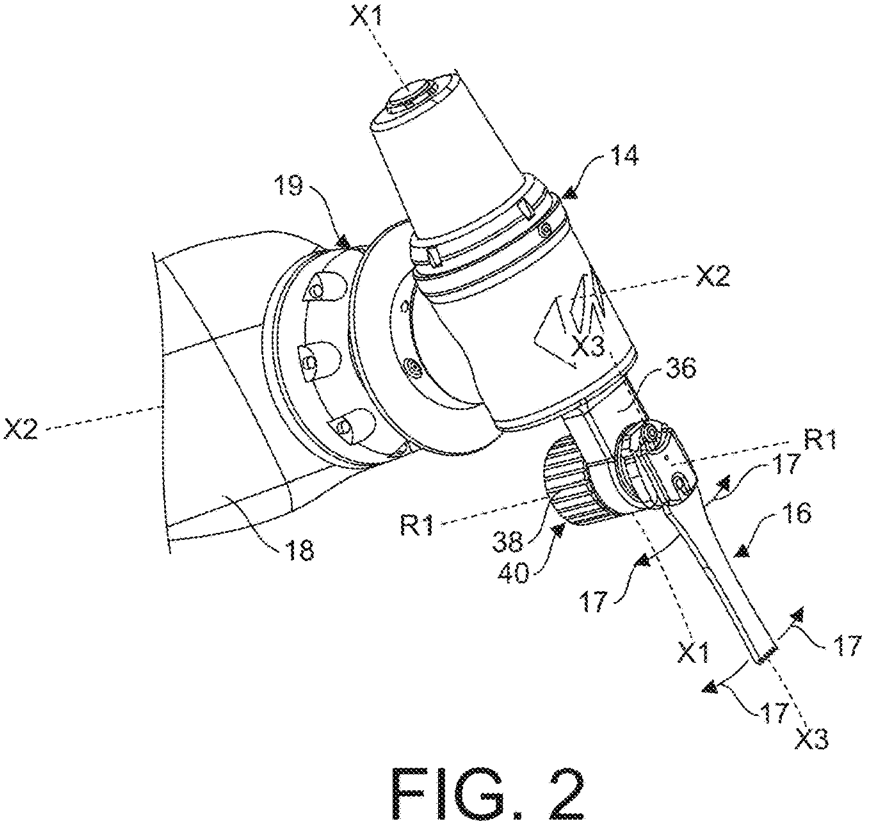
FIG. 2 illustrates, in one example, an elevational perspective view of a distal arm segment, end effector and cutting tool of the surgical robot of FIG. 1, in accordance with one or more aspects of the present disclosure.

As shown in FIG. 2, the end effector 14 may be rotatably coupled to an end, last or termination segment 18 of the articulated arm 12 via a rotatable connector assembly 19 therebetween. The rotatable connector assembly 19 may be configured such that the end effector 14 is rotatable about the axis X2-X2 of the end arm segment 18. As shown in FIGS. 1 and 2, and discussed further below, the end effector 14 may be configured such that the axis X2-X2 of the end arm segment 18 and the longitudinal axis X1-X1 of the end effector 14 (and the longitudinal axis X3-X3 of the cutting tool 16), are angled with respect to each other. In the illustrated exemplary embodiment, the longitudinal axis X1-X1 of the end effector 14 (and the longitudinal axis X3-X3 of the cutting tool 16, as well as the cutting direction/pathway 17 of the cutting tool 16 along which it is configured to cut) and the axis X2-X2 of the end arm segment 18 are oriented substantially perpendicular to each other, and may intersect with each other. As also shown in FIGS. 1 and 2, the end effector 14 may form a generally cylindrical shape (or varying diameter along the longitudinal axis X1-X1) about the longitudinal axis X1-X1, and may be extended along the longitudinal axis X1-X1 (i.e., define a total length along the longitudinal axis X1-X1 that is greater than the maximum width/diameter thereof). The cylindrical shape may be advantageous for reducing and/or mitigating vibrations (e.g., via a torsional mass damper, for example).

Referring further to FIG. 1, since the position, orientation, and motion of the plurality of joints and the plurality of arm segments relative to the base may be defined, and the angular orientation of the end effector 14 with respect to the end arm segment 18 of the articulated arm 12, the position and orientation of the cutting tool 16 extending from the end effector 14 can be calculated or determined by the robotic system 10. As another example, the position and orientation of the cutting tool 16 extending from the end effector 14 can be determined via an imaging system. It is understood that the exemplary illustrative cutting tool 16 is configured for cutting bone or other tissue, however the cutting tool 16 may be replaceable with a different cutting tool or a non-cutting implements that may function as, for example, a marking device or a viewing device.

Figure 3:
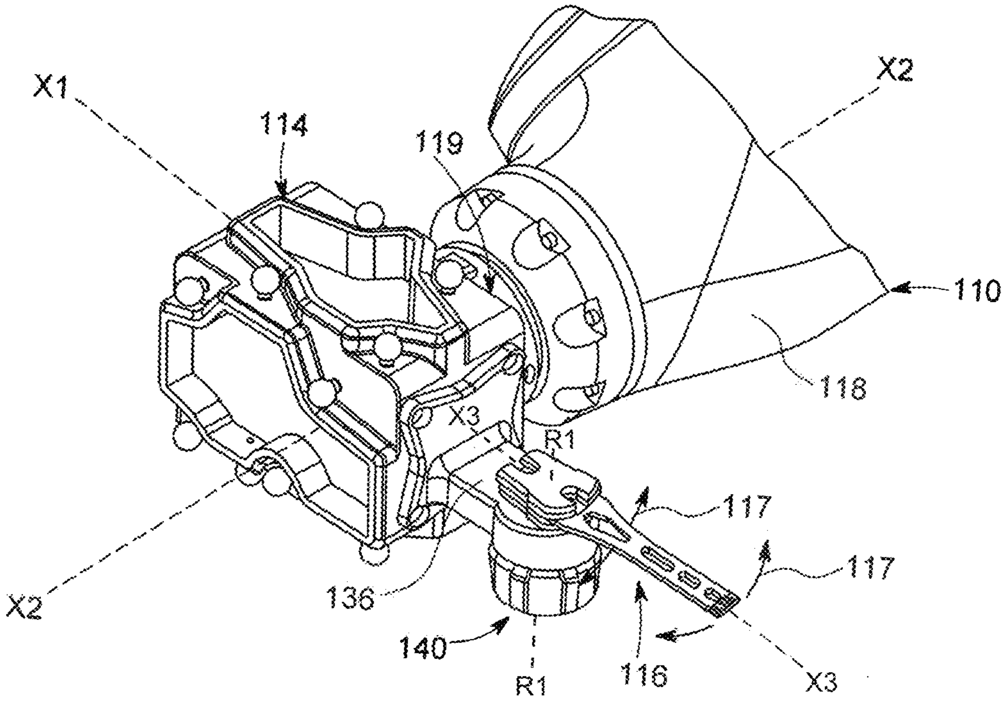
FIG. 3 illustrates, in another example, an elevational perspective view of a distal arm segment, end effector and cutting tool of a surgical robot, in accordance with one or more aspects of the present disclosure.
Figure 4:
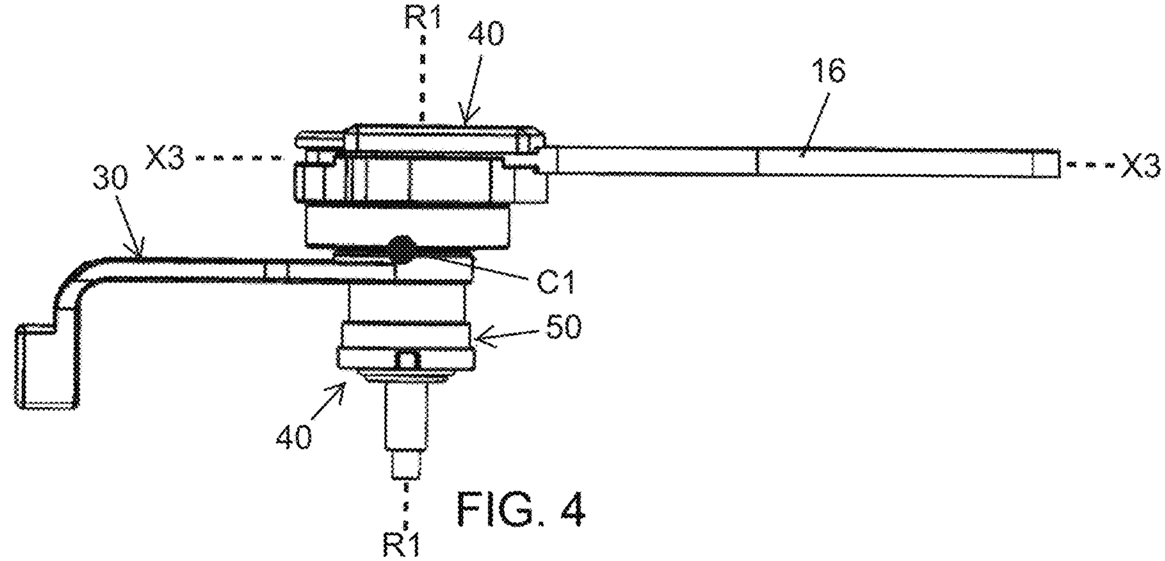
FIG. 4 illustrates, in one example, a side view of an assembly of a mounting arm and an attachment mechanism of the end effector, and the cutting instrument, of the surgical robot of FIG. 2, in accordance with one or more aspects of the present disclosure.
Figure 5:
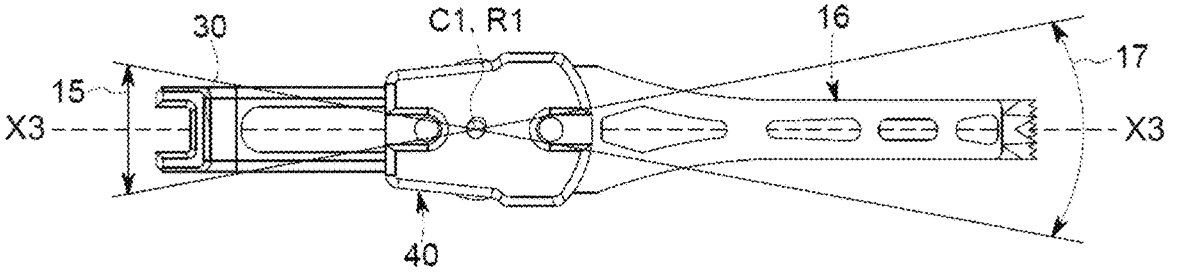
FIG. 5 illustrates, in one example, a top view of the assembly of the mounting arm, the attachment mechanism and the cutting instrument of FIG. 4, in accordance with one or more aspects of the present disclosure.

As shown in FIGS. 2-5, 7 and 8, the cutting tool 16 may be a saw blade that has a thin, flat, elongated shape with a cutting edge 23 at a distal tip or end portion 22 of a blade body portion 24. The thin, flat design may minimize the size of the blade's kerf and allow the blade to make an accurate, straight cut. The cutting edge 23 may be generally oriented along a direction that is orthogonal to the direction of blade elongation and contains a plurality of teeth and/or abrasives. Thus, when the blade 16 is translated along a cut pathway, the cutting edge 23 can be pressed against the surface of the bone or other tissue that requires resection as it is translated along its cutting pathway or direction 17. The saw blade 16 is provided with cutting teeth that extend forward from the distal end 22 of the blade body 24, as shown in FIGS. 4 and 5.

Figure 7:
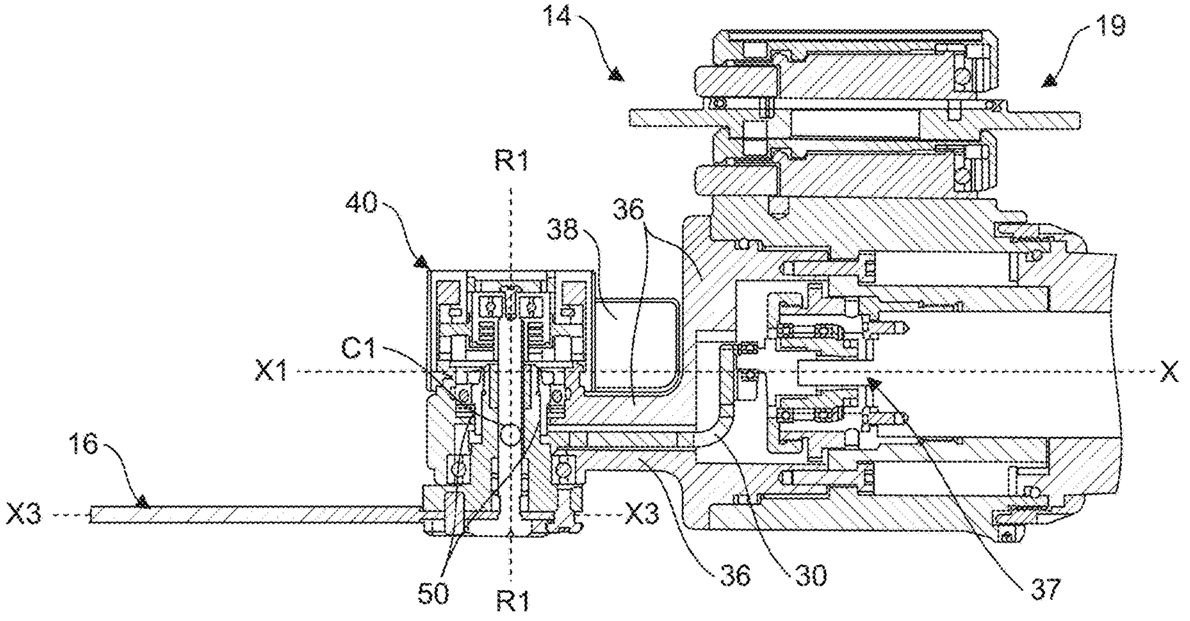
FIG. 7 illustrates, a side cross-sectional view of a portion of the end effector including the mounting arm, the reinforcement collar and the attachment mechanism, and a portion of the cutting instrument, of the surgical robot of FIG. 2, in accordance with one or more aspects of the present disclosure.

As shown in FIG. 7, the cutting tool saw blade 16 includes an attachment, tang or hub portion 20 at a proximal end portion. The attachment portion 20 may be configured to attach with an attachment mechanism 40 of the end effector 14, as shown in FIGS. 2-5 and 7. For example, the end effector 14 may include a chuck or other attachment mechanism 40 configured to mate with the attachment portion 20 and removably secure the saw blade 16 (or other cutting tool) and the end effector 14 together. The axis X3-X3 of the cutting tool saw blade 16 may extend through the attachment portion 20, the body portion 24 and the tip portion 22 (and thus the cutting edge 23), and the cutting blade 16 may be longitudinally extended along the axis X3-X3. As explained further below, the cutting blade 16 may be substantially symmetrically configured about the axis X3-X3 at least along the lateral direction extending perpendicular to the axis X3-X3 (and lying along the plane of the blade 16).

The cutting tool 16 (e.g., at least the cutting edge 23 thereof) may be configured to cut when moved/translated in a cutting pathway 17, such as in a reciprocating motion (along forward and/or back strokes), along a linear direction (colinear with the cutting edge), along a plane (e.g., two dimensions) or in a three-dimensional pattern. The exemplary illustrative cutting blade 16 shown in FIGS. 2-5, 7 and 8, is configured to be pivoted back and forth, or oscillated, in a cutting pathway 17 that extends along the plane in which the blade 16 is oriented and is orthogonal to the direction of blade elongation. The cutting blade 16 may be designed such that the cutting direction or pathway 17 oscillates linearly laterally or in an arc extended along the plane of the blade 16. The blade 16 may thereby be configured as a sagittal saw blade. In some other embodiments, the cutting tool 16 may comprise a blade that is configured to cut while moving back and forth along the longitudinal axis X3-X3, or a tool that is configured to cut while rotating about the axis X3-X3.

As explained further below, the surgical robot 10 is configured to prevent and/or mitigate the generation of vibrations that pass through the articulated arm 12, the end effector 14 and/or the cutting blade 16 (and the subcomponents thereof). The surgical robot 10 prevents and/or mitigates the likelihood that any vibrations that are generated are adequately controlled such that the robot 10 can maintain control of the cut path of the cutting tool 16 along an intended path. The surgical robot 10 is also configured to prevent and/or mitigate the likelihood of damage and/or failure thereof via vibrations that are generated. The vibration prevention and mitigation features of the surgical robot 10 thereby provide for safe, accurate and reliable cutting of tissue (e.g., bone and/or soft tissue) via the cutting tool 16. Still further, due to the vibration prevention and mitigation features, the surgical robot 10 may be configured to operate fully autonomously such that the robot 10 executes predetermined/programmed surgical cuts (via following preplanned cut paths stored in memory) without a user physically moving the end effector 14 and cutting tool 16. It is noted that the vibration prevention and mitigation features of the robot 10 may be utilized individually, or in combination (e.g., all or some) in a particular robot (or robotic system) or related robotic method.

In some embodiments, the vibration prevention and mitigation features of the surgical robot 10 may comprise vibration prevention/mitigation instrument design, vibration prevention/mitigation instrument mounts, vibration prevention/mitigation instrument operation (such as, but not limited to, vibration prevention/mitigation optimizations of tool motion), and vibration prevention/mitigation add-on components (such as, but not limited to, tuned mass dampers).

With reference to FIGS. 2-8, in some embodiments, the end effector 14 of the robot 10 may be configured to oscillate (i.e., translate in a back and forth manner) the cutting tool 16, which is configured as a cutting blade, along an oscillatory cutting direction or pathway 17. As explained above, the cutting tool 16 may be configured as a sagittal cutting blade, and the oscillatory cutting pathway 17 may extend along a plane defined by the blade. When the cutting tool is configured as a sagittal saw blade, the blade performs a cutting action by being translated along the longitudinal axis X3-X3 (e.g., via the articulated arm 12, at least in part) in a direction extending from the coupling portion 20 to the tip portion 22 as the blade (and the cutting teeth 23 thereof) is being oscillated along the oscillatory cutting pathway 17 (i.e., in cutting strokes). Because of the motion along the oscillatory cutting pathway 17 applied by the end effector 14, and the forward pressure applied by the robot 10 (e.g., via the articulated arm 12, at least in part), the teeth 23 of the cutting tool 16 cut and separate material (e.g., tissue, such as bone tissue).

The oscillatory cutting pathway 17 may define an oscillation axis R1-R1 about which the oscillation occurs, as shown in FIG. 4. The oscillation axis R1-R1 thereby represents the center of the oscillatory cutting pathway 17 halfway between the extreme opposing ends or amplitudes of the back and forth motion of the cutting tool 16. The oscillatory cutting pathway 17 may be linear, or may be a curved or an arced pathway defined by a radius that extends from a rotation point or axis R1-R1 thereof as shown in FIGS. 4 and 5. The oscillatory cutting pathway 17 and the longitudinal axis X3-X3 of the blade 16 (and thus the oscillation axis R1-R1 of the oscillatory cutting pathway 17) may thereby be oriented substantially perpendicular with respect to each other. In some embodiments, the oscillation/rotation axis R1-R1 may lie along the longitudinal axis X3-X3 of the blade 16, and the oscillation/rotation axis R1-R1 may be oriented perpendicular to the longitudinal axis X3-X3 of the blade 16 and the longitudinal axis X1-X1 of the end effector 14. In some embodiments, the oscillation/rotation axis R1-R1 may be oriented substantially parallel to axis X2-X2 of the end arm segment 18, and/or lie along (i.e., intersect with) the longitudinal axis X3-X3 of the blade 16 and the longitudinal axis X1-X1 of the end effector 14.

In some embodiments, the oscillatory cutting pathway 17 may extend along a plane that is oriented substantially parallel to the longitudinal axis X3-X3 of the blade 16 and substantially parallel to the longitudinal axis X1-X1 of the end effector 14, as shown in FIG. 2. As shown in FIG. 2 the oscillatory cutting pathway 17 may extend along a plane that is oriented substantially normal to the axis X2-X2 of the end arm segment 18, and as shown in FIGS. 4 and 5 the oscillatory cutting pathway 17 may extend along a plane that is oriented substantially normal to the oscillation/rotation axis R1-R1 of the blade 16 (and the end arm segment 18). It is noted that such an arrangement may unexpectedly advantageously reduce the vibratory forces effecting the robotic system 10 (e.g., total amount of vibrations and/or their magnitude, for example), and/or result in less deleterious vibratory wear on the components of the robotic system 10.

Another exemplary surgical robotic system 110 that is shown in FIG. 3 that includes the end effector 114 oriented differently than the orientation of the end effector 14 of the surgical robotic system 10 of FIGS. 1 and 2. The surgical robot 110 of FIG. 3 is substantially similar to the surgical robot 10 described herein, and therefore like reference numerals preceded with “1” are used to indicate like components, aspects, portions, functions, processes and the like, and the description above directed to thereto equally applies, and is not repeated for brevity and clarity purposes.

The surgical robot 110 differs from the surgical robot 11 in the orientation of the robotic arm and end effector. As shown in FIG. 3, the robotic arm 112 and the end effector 114 of the surgical robot 110 are configured such that the oscillation/rotation axis R1-R1 is oriented substantially perpendicular to the axis X2-X2 of the end arm segment 118. Accordingly, the oscillatory cutting pathway 17 extends along a plane that is oriented substantially parallel to the axis X2-X2 of the end arm segment 18. It is noted that other relative orientations of the robotic arm 112 (and in particular the end arm segment 118 thereof) and the end effector 114 of the surgical robot 110 may be employed.

Figure 10:
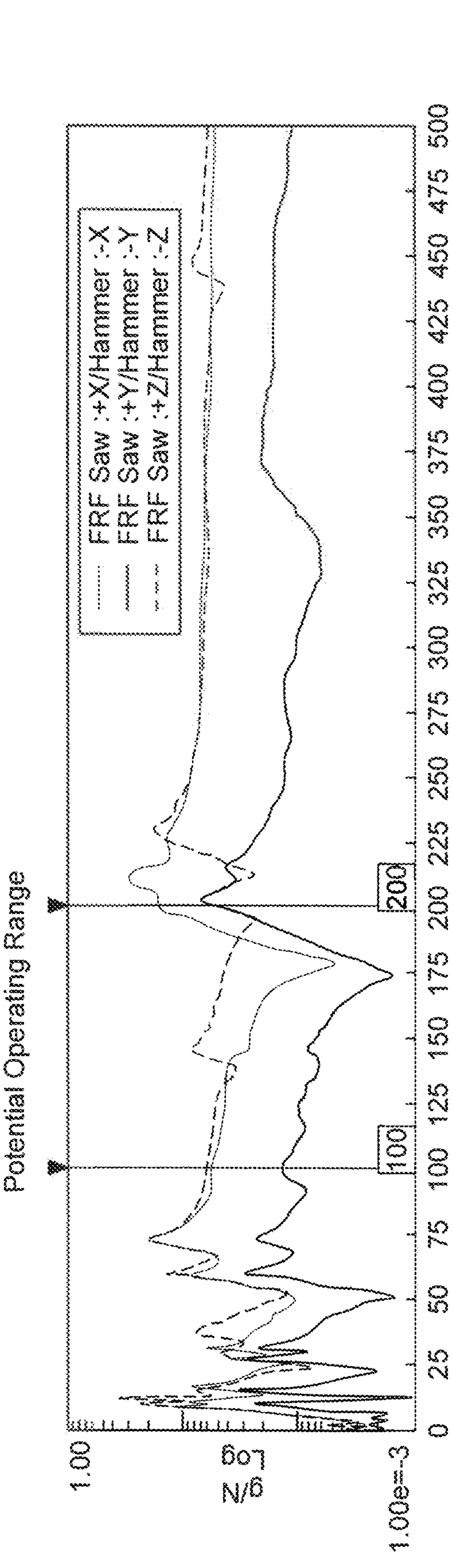
FIG. 10 illustrates, in one example, a graph of the vibrations detected via the natural frequency evaluation of FIG. 9, in accordance with one or more aspects of the present disclosure.
Figure 11:
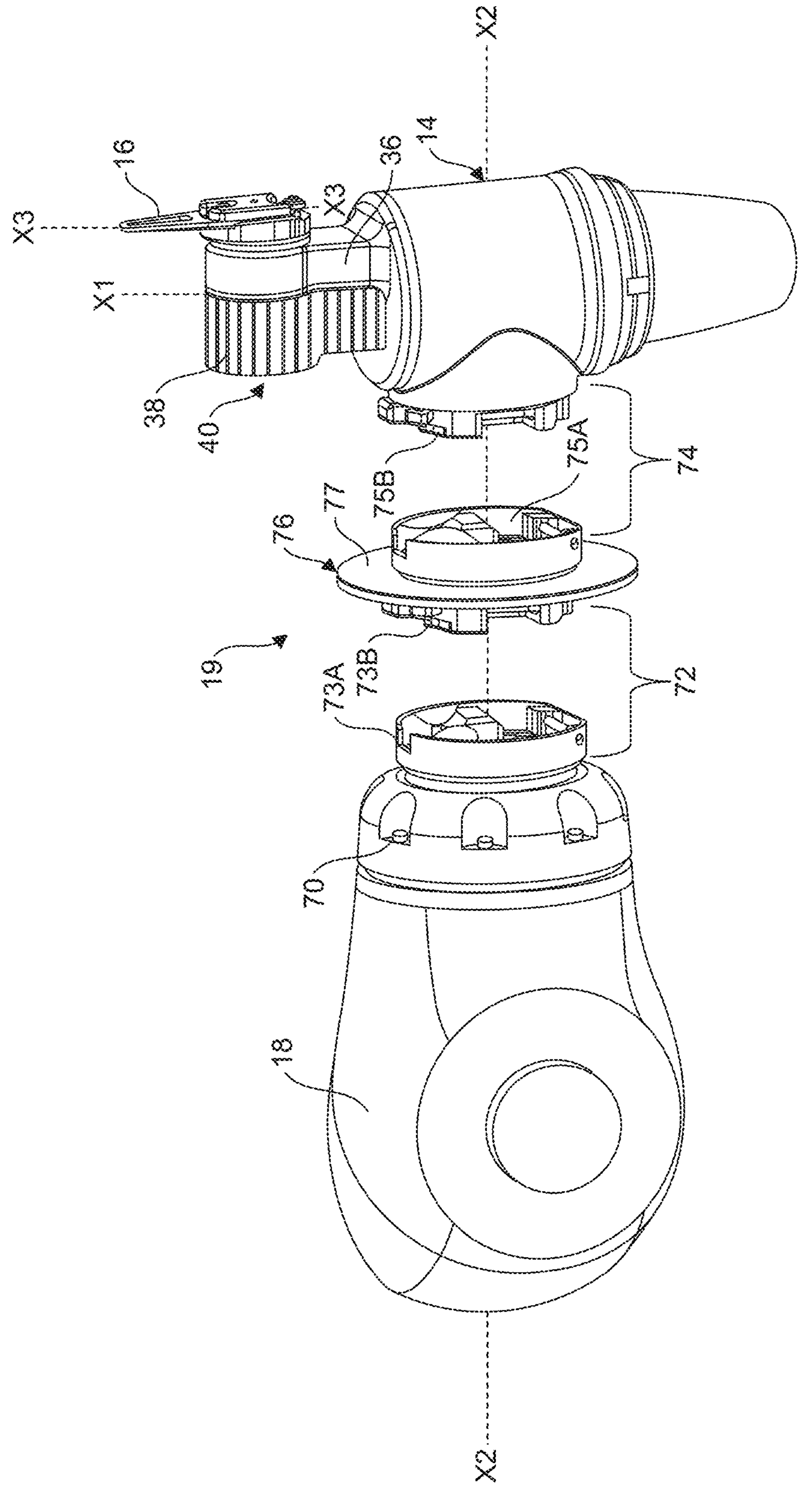
FIG. 11 illustrates, in one example, an exploded perspective view of the end arm segment, connector assembly and end effector of the surgical robot of FIG. 1, in accordance with one or more aspects of the present disclosure.
Figure 12:
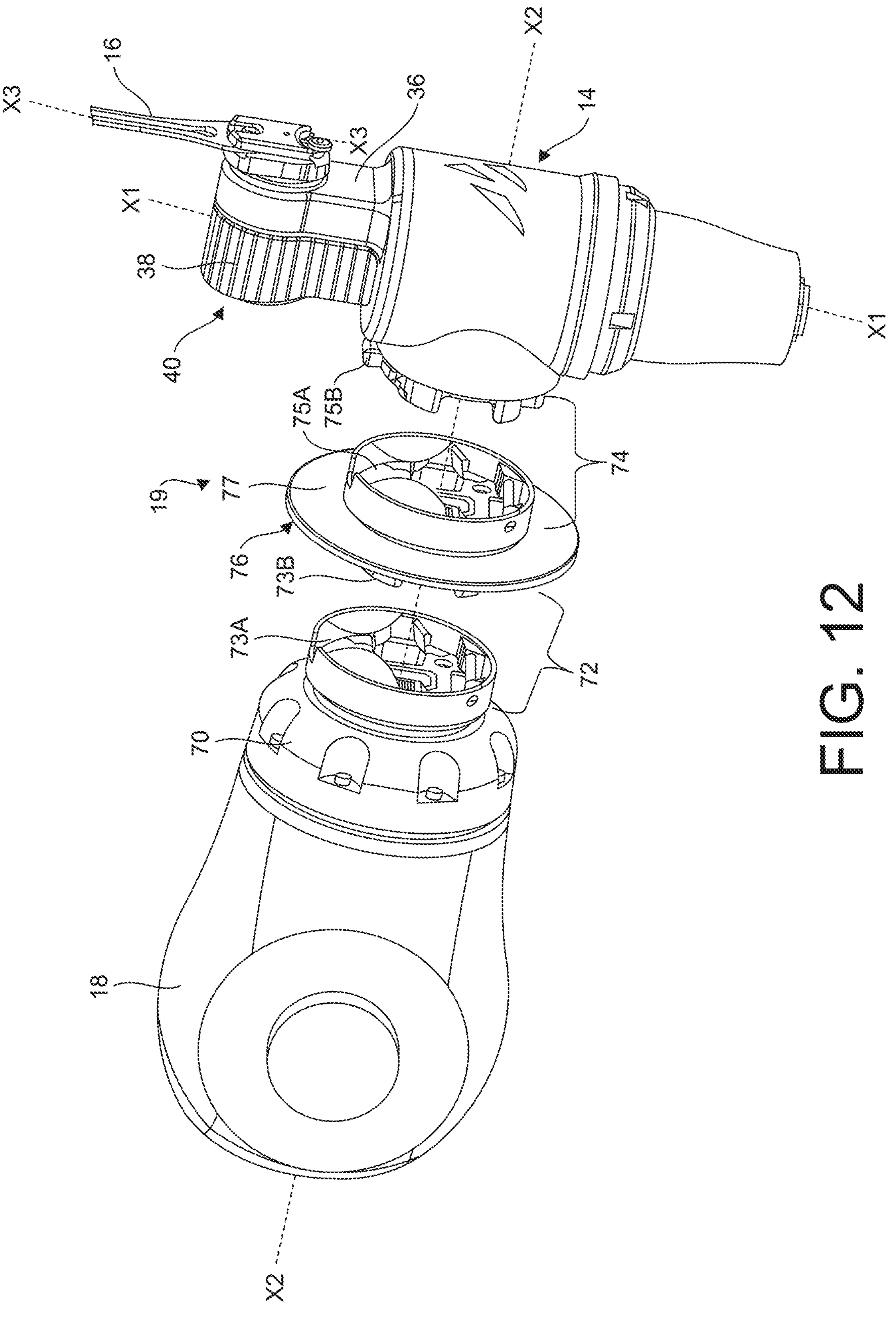
FIG. 12 illustrates, in one example, another exploded perspective view of the end arm segment, connector assembly and end effector of the surgical robot of FIG. 1, in accordance with one or more aspects of the present disclosure.

As shown in FIGS. 4 and 10, the attachment mechanism 40 is configured to securely and reliably removably couple the cutting tool 16 and the end effector 14 together. The attachment mechanism 40 may be part of, or attached to, the end effector 14. As shown in FIG. 7, the attachment mechanism 12 may be configured to engage faces or sides of the cutting tool 16 (e.g., opposing faces), and potentially apply a compressive force thereto. The adjustment member 38 may thereby be utilized (e.g., manually) by a user to effectuate the clamping mechanism, and thereby “open” the clamping members by enlarging the space between the engagement surfaces thereof, or “close” the clamping members by minimizing the space between the engagement surfaces. In some embodiments, the clamping mechanism may be configured to adjust (e.g., manually) the distance between the engagement surfaces along a direction that extends normal to the plane of the cutting tool 16, for example. It is noted, however, that the attachment mechanism 40 may comprise any configuration that securely couples the cutting tool 16 and the end effector 14 together such that the end effector 14 effectuates motion of the cutting tool 16 along the cutting pathway 17.

As shown in FIGS. 4-7, the end effector 14 may include an attachment arm 30 that is coupled to (directly or indirectly), and longitudinally extends from, a portion of drive or motion portion 37 of the end effector 14. The attachment arm 30 may also be coupled to (directly or indirectly) to the attachment mechanism 40. The attachment arm 30 may thereby couple (directly or indirectly) and extend longitudinally between (at least partially) the drive portion 37 of the end effector 14 and the attachment mechanism 40, such as along the longitudinal axis X3-X3 of the cutting tool 16 and the longitudinal axis X1-X1 of the end effector 14. The drive portion 37 of the end effector 14 is the mechanism that provides physical motion (e.g., oscillation) that, ultimately, effectuates motion (e.g., oscillation) of the cutting tool 16 along the cutting pathway 17. As noted above, the drive portion 37 may comprise a motor or other device or system that produces physical motion, as shown in FIG. 7.

As shown in FIG. 7, in some embodiments, the attachment arm 30 may be positioned within an internal cavity of a housing 36 that longitudinally extends from a portion of the end effector 14. In some embodiments, the housing 36 may be fixedly coupled to the end effector 14 such that the housing 36 does not translate with respect to end effector 14 itself via the drive portion 37. In this way, the housing 36 may not be translated along the cutting pathway 17 and/or a motion pathway 15 of the attachment arm 30 as shown in FIG. 5, and as explained further below. For example, the drive portion 37 may be configured to translate the attachment arm 30 along an attachment pathway (e.g., oscillatory pathway) 15 within the housing 36, such that the housing 36 is not translated along the attachment pathway 15 (i.e., the attachment arm 30 may translate with respect to the housing 36). In some alternative embodiments, the housing 36 may be coupled to the end effector 14 such that the housing 36 is translated with respect to end effector 14 itself via the drive portion 37. For example, in some such alternative embodiments, the housing 36 may be translated along the cutting pathway 17 and/or the attachment pathway 15 of the attachment arm 30 via the drive portion 37.

As shown in FIGS. 2 and 7, the attachment mechanism 40 may be coupled with a longitudinal end portion of the housing 36. The housing 36 may fix the position (e.g., longitudinal, lateral and height positions) of the attachment mechanism 40 as a whole with respect to the end effector 14 as a whole, and in particular with respect to the drive portion 37. It is noted that at least some portions of the attachment mechanism 40 may be able to rotate about and/or translate along a height direction extending perpendicular to the longitudinal and lateral directions. The attachment arm 30 and the attachment mechanism 40, and thereby the cutting tool 16 (when coupled with the attachment mechanism 40), may be fixed together such that motion of the attachment arm 30 along the attachment pathway 15 (e.g., laterally) effectuates motion of the cutting tool 16 along the cutting pathway 17 (e.g., laterally). For example, the attachment mechanism 40 may be configured such that the housing 36 fixes the location of a shaft that defines an axis that is aligned (or defines) the axis of rotation R1-R1. A coupling end portion 35 of the attachment arm 30 may be coupled and rotatable fixed to the shaft. In this way, the drive portion 37 causes a drive coupling end portion 33 of the attachment arm 30 that is attached to the drive portion 37 to reciprocate along the attachment pathway 15, and the coupling end portion 35 to rotate the shaft, and thus the attachment mechanism 40 components that are coupled to the cutting tool 16, about the axis of rotation R1-R1 such that the cutting tool 16 is reciprocated about the cutting pathway 17.

In some embodiments, as shown in FIGS. 4 and 5, the attachment pathway 15 of the attachment arm 30 and the cutting pathway 17 of the cutting tool 16 may mirror each other longitudinally across the axis of rotation R1-R1. In some such embodiments, the axis of rotation R1-R1 may be defined by the attachment mechanism 40, such as the attachment arm 30 and/or the reinforcement collar/sleeve 50. As noted above, the housing 36 may fix the longitudinal and lateral position of the attachment mechanism 40. A center or axis of oscillation X3-X3 of the attachment pathway 15 of the attachment arm 30 and the cutting pathway 17 of the cutting tool 16 may thereby be aligned and pass through the axis of rotation R1-R1, as shown in FIG. 4. Lateral motion of the attachment arm 30 along the attachment pathway 15 in a first lateral direction thereby effectuates lateral motion of the cutting tool 16 along the cutting pathway 17 in a second lateral direction that opposes the first lateral direction. Thus, oscillation of the attachment arm 30 via the drive portion 37 of the end effector 14 effectuates oscillation of the cutting tool 16 along the cutting pathway 17.

In some embodiments, at least the attachment arm 30 of the end effector 16 and the cutting tool 16 (e.g., a sagittal saw/cutting blade) are configured to mitigate vibration caused by the oscillation thereof via the mass displacement thereof. In some such embodiments, to mitigate vibration caused by the oscillation of the end effector 14 and the cutting tool 16, at least the attachment arm 30 and the cutting tool 16 are substantially mass balanced across the axes of oscillation X3-X3 thereof (and across the longitudinal axes X1-X1). For example, via weight optimization of the attachment arm 30, the center of mass of the attachment arm 30 may be positioned along or substantially aligned with the axis of oscillation X3-X3 thereof. In some embodiments, the center of mass of the attachment arm 30 may be positioned along or substantially aligned with the longitudinal axis X1-X1 (in a neutral or center position thereof along the attachment pathway 15). In some embodiments, the physical configuration of the attachment arm 30 may be mirrored laterally across the longitudinal axis X1-X1. Similarly, the center of mass of the cutting tool 16 may be positioned along or substantially aligned with the axis of oscillation X3-X3 thereof. In some embodiments, via weight optimization of the cutting tool 16, the center of mass of the cutting tool 16 may be positioned along or substantially aligned with the longitudinal axis X1-X1 (in a neutral or center position thereof along the cutting pathway 17). In some embodiments, the physical configuration of the cutting tool 16 may be mirrored laterally across the longitudinal axis X1-X1. It is noted that any other components of the end effector 14, including the attachment mechanism 40, that may oscillate during operation of the robot 10, may be configured such that the center of mass thereof is substantially mass balanced along the axis of oscillation thereof. In some embodiments, the centers of mass of the attachment arm 30 and the cutting tool 16 are respectively positioned within 10%, or within 8%, or within 6%, or within 5%, or within 4%, or within 3%, or within 2%, or within 1% of the total/maximum size thereof extending along the attachment pathway 15 or cutting pathway 17 (e.g., extending in the lateral direction), respectively, from the axes of oscillation X3-X3.

As shown in FIGS. 4, 5 and 7, via weight optimization of the attachment arm 30 and the cutting tool 16, in some embodiments the center of mass Cl of the attachment arm 30 and the cutting tool 16 in combination may be positioned along or substantially aligned with the axis of oscillation X3-X3 thereof. In some embodiments, the center of mass Cl of the attachment arm 30 and the cutting tool 16 in combination may be positioned along or substantially aligned with the longitudinal axis X1-X1 (in a neutral or center position thereof along the attachment pathway 15 and the cutting pathway 17). In some embodiments, via weight optimization of at least the attachment arm 30 and the cutting tool 16, the center of mass Cl of the attachment arm 30, the attachment mechanism 40 and the cutting tool 16 in combination may be positioned along or substantially aligned with the axis of oscillation X3-X3 of the attachment arm 30 and the cutting tool 16. In some embodiments, the center of mass Cl of the attachment arm 30, the attachment mechanism 40 and the cutting tool 16 in combination may be positioned along or substantially aligned with the longitudinal axis X1-X1 (in a neutral or center position thereof along the attachment pathway 15 of the attachment arm 30 and the cutting pathway 17 of the cutting tool 16). In some embodiments, the center of mass of the attachment arm 30, attachment mechanism 40 and cutting tool 16 construct is positioned within 10%, or within 8%, or within 6%, or within 5%, or within 4%, or within 3%, or within 2%, or within 1% of the maximum size thereof extending along the attachment pathway 15 and cutting pathway 17 (e.g., extending in the lateral direction), respectively, from the axes of oscillation X3-X3 and/or the axis of rotation R1-R1.

In some embodiments, at least the attachment arm 30 of the end effector 16 and the cutting tool 16 (e.g., a sagittal saw/cutting blade) are configured to mitigate vibration caused by the oscillation thereof via the total mass thereof. For example, to reduce the amplitude of the vibratory forces/motions transferred to aspects if the robot 10, at least the attachment arm 30 of the end effector 16 and the cutting tool 16 (e.g., a sagittal saw/cutting blade) are configured such that their total mass is minimized. It is noted that any other oscillating components of the end effector 16 (including the attachment mechanism 40) or robotic arm 12, for example, may also be configured to minimize the total mass thereof to thereby minimize the amplitude of the vibratory forces/motions caused thereby during oscillation.

Figure 6:
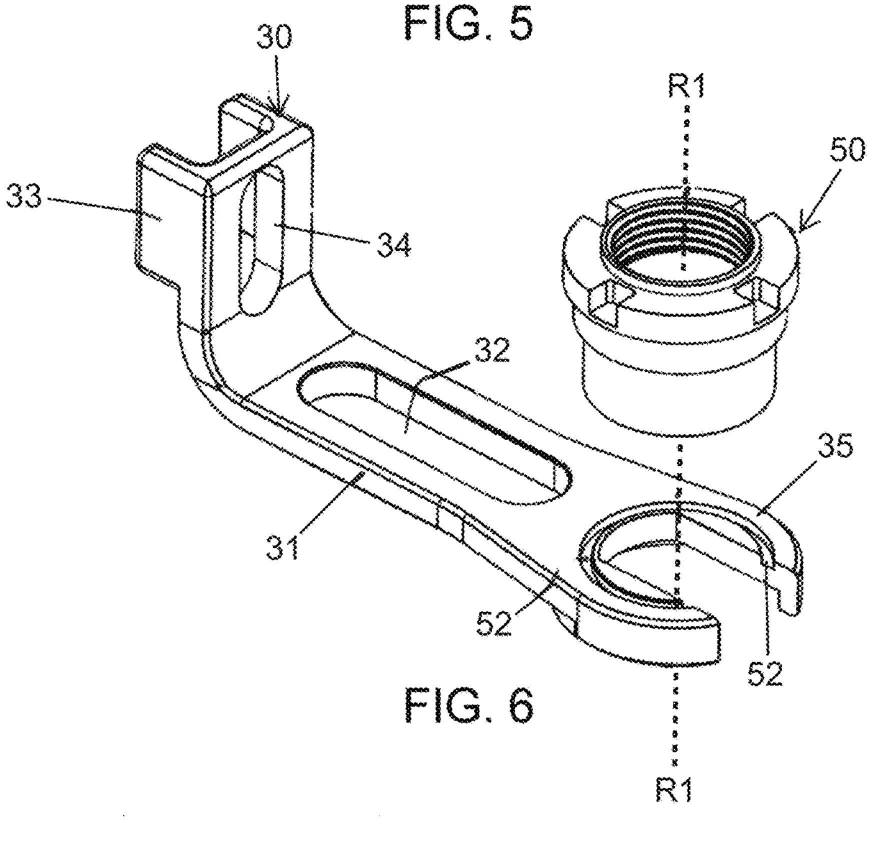
FIG. 6 illustrates, in one example, an elevational perspective exploded view of the mounting arm and a reinforcement collar of the end effector of FIG. 4, in accordance with one or more aspects of the present disclosure.

As shown in FIG. 6, in some embodiments, the attachment arm 30 may comprise a proximal or drive coupling end portion 33, a distal cutting tool coupling end portion 35 and a body portion 31 extending longitudinally between the drive coupling end portion 33 and the cutting tool coupling end portion 35. The drive coupling end portion 33 may thereby define one longitudinal end of the attachment arm 30, and the cutting tool coupling end portion 35 may define the other longitudinal end of the attachment arm 30, as shown in FIG. 5. The attachment arm 30 may be extended or elongate along the longitudinal direction (i.e., longer along the longitudinal direction than its width along the lateral direction).

In some embodiments, the drive coupling end portion 33 may be angularly offset (but essentially longingly aligned) from the body portion 31 and the cutting tool coupling end portion 35, as shown in FIG. 6. For example, the body portion 31 and the cutting tool coupling end portion 35 may extend (or be oriented) longitudinally (e.g., linearly), and the drive coupling end portion 33 may be angled (extend/oriented) substantially perpendicularly thereto. As discussed above, the drive coupling end portion 33 may be configured to couple with the drive portion 37 of the end effector.

The cutting tool coupling end portion 35 may be configured to couple with the attachment mechanism 40. For example, as shown in FIG. 6, the cutting tool coupling end portion 35 may include an axial/longitudinal slot extending from the free end thereof. The side walls of the axial/longitudinal slot may engage a non-circular (e.g., straight-sided) shaft or otherwise engage a portion of the attachment mechanism 40 such that movement of the attachment arm 30 along the attachment pathway 15 via the drive portion 37 causes the cutting tool 16 to be translated along the cutting pathway 17, as shown in FIGS. 6 and 7. In other words, the cutting tool coupling end portion 35 may drivingly engage a portion of the attachment mechanism 40 to apply a torque thereto about the oscillation axis R1-R1.

As also shown in FIGS. 6 and 7, the coupling end portion 35 of the attachment arm 30 may include a retention recess or groove 52 extending around the free end opening/slot that mates with the reinforcement sleeve or collar 50. An axial end of the reinforcement collar 50 thereby resides within the retention groove 52 and strengthens the coupling end portion 35. In some such embodiments, the reinforcement collar 50 may provide necessary strength to the coupling end portion 35 such that it properly withstands torsional and vibratory forces during cutting operations.

The reinforcement collar 50 may define an inner aperture or through hole that is substantially aligned with the free end opening/slot and the oscillation axis R1-R1. In some embodiments, the inner aperture of the reinforcement collar 50 may act to define the oscillation axis R1-R1. The attachment mechanism 40 may include components that mate/couple with the reinforcement collar 50 and form/operate the selective clamping of the cutting tool 16 with the end effector 14. For example, the attachment mechanism 40 may include a clamping shaft that extends axially through/within the inner aperture of the reinforcement collar 50, and a manually operated knob or lever mounted (directly or indirectly) on the reinforcement collar 50 that rotates the clamping shaft (or rotates a component on the shaft) and, thereby, causes axial movement of one or more cutting tool clamping members. In some embodiments, during movement of the attachment arm 30 along cutting pathway 17 about oscillation axis R1-R1, the reinforcement collar 50 may be rotated about the oscillation axis R1-R1 via the attachment arm 30 (i.e., the attachment arm 30 and the reinforcement collar 50 may be rotationally fixed). In some other embodiments, during movement of the attachment arm 30 along cutting pathway 17 about oscillation axis R1-R1, the reinforcement collar 50 may remain stationary (e.g., via being coupled to the housing 36) such that the coupling end portion 35 slides over the reinforcement collar 50 via the retention slot.

As described above, in some embodiments, the end effector 14 may be configured such that the attachment arm 30 and the cutting tool 16 are fixed together, and rotate about a rotation axis R1-R1. In such embodiments, the cutting tool coupling end portion 35 may engage and rotate a portion of the attachment mechanism 40 that defines or forms the rotation axis R1-R1 (e.g., a rotation shaft). In some other embodiments, the end effector 14 may be configured such that the attachment arm 30 directly translates the cutting tool 16 along the cutting pathway 17 (i.e., the attachment pathway 15 is the same as the cutting pathway 17).

As shown in FIG. 6, the attachment arm 30 of the end effector 16 may include at least one aperture or cavity to minimize the total mass thereof, and thereby minimize the amplitude of any vibratory forces/motions caused by the attachment arm 30 during oscillation thereof. For example, in some embodiments, the drive coupling end portion 33 may include at least one aperture 34, which may be configured as at least one through hole, as shown in FIG. 6. In some embodiments, the body portion 31 of the attachment arm 30 may include at least one aperture or cavity to minimize the total mass thereof, and thereby minimize the amplitude of any vibratory forces/motions caused by the attachment arm 30 during oscillation thereof. For example, in some embodiments, the body portion 31 may include at least one aperture 32, which may be configured as at least one through hole, as shown in FIG. 6. The at least one aperture 32 in the body portion 31 may be extended or elongate along the axial/longitudinal direction, as shown in FIG. 6. In some embodiments, the at least one aperture or cavity of the attachment arm 30 may be centered on a longitudinal axis of the attachment arm 30.

Figure 8:
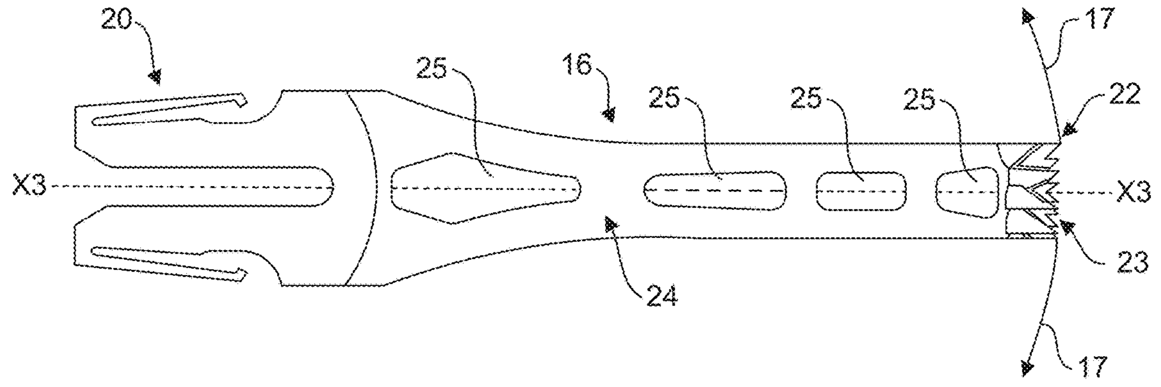
FIG. 8 illustrates, in one example, a top view of the cutting tool of the surgical robot of FIG. 1, in accordance with one or more aspects of the present disclosure.

As shown in FIG. 8, the cutting tool 16 (e.g., a sagittal saw blade) may include at least one aperture or cavity 25 to minimize the total mass thereof, and thereby minimize the amplitude of any vibratory forces/motions caused by the cutting tool 16 during oscillation thereof. For example, in some embodiments, the cutting tool 16 may be configured with the attachment portion 20 a one longitudinal/axial end, the cutting portion at the one longitudinal/axial end, and a body portion 24 longitudinally/axially extending therebetween that includes one aperture or cavity 25. For example, as shown in FIG. 8, the body portion 24 of the cutting tool 16 may include a plurality of axially/longitudinally spaced through holes 25. At least one of the axially/longitudinally spaced through holes 25 may be extended or elongate along the axial/longitudinal direction, as shown in FIG. 8. In some embodiments, the at least one aperture or cavity 25 of the cutting tool 16 may be centered on a longitudinal axis X3-X3 of the cutting tool 16.

Figure 9:
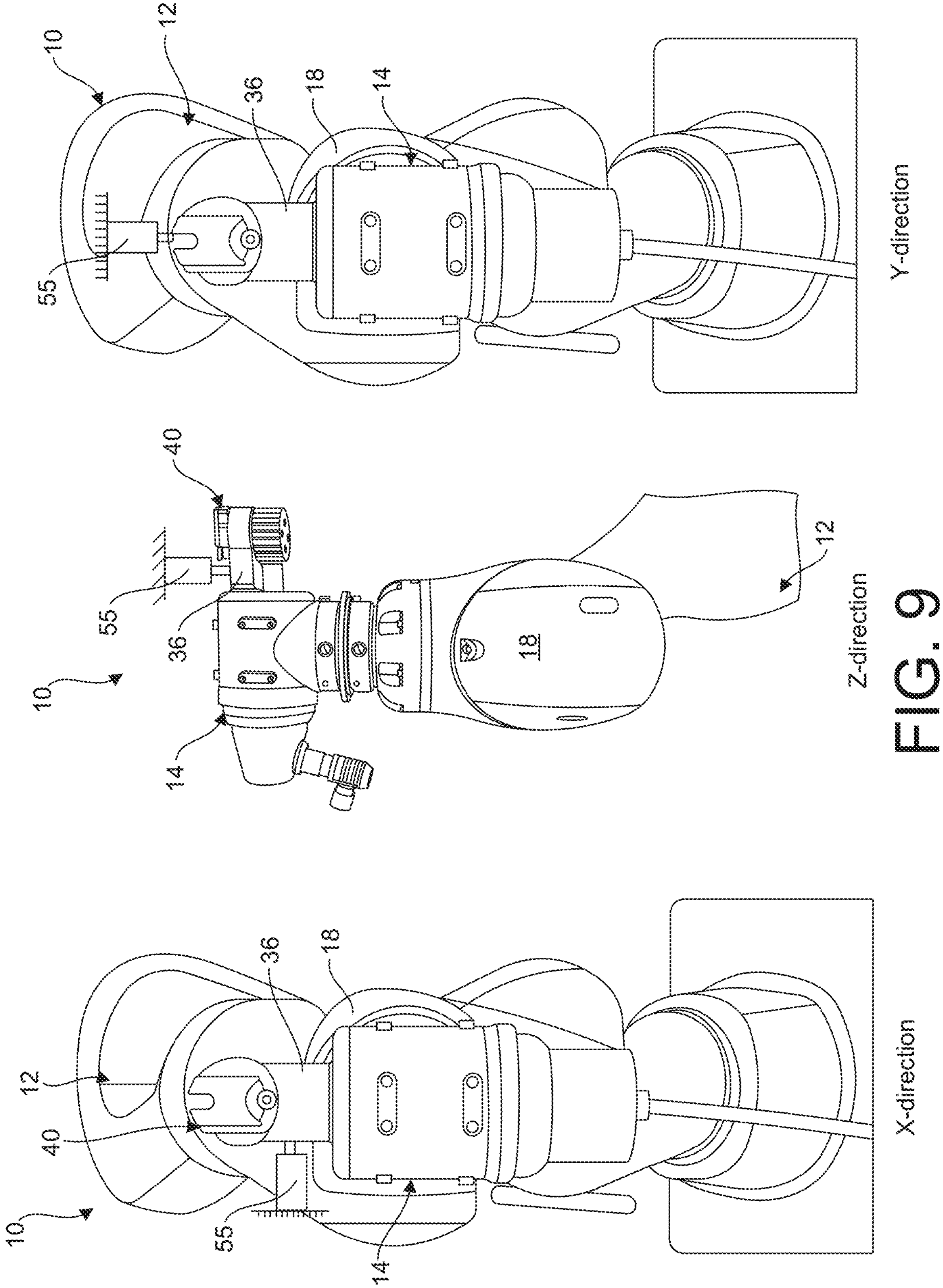
FIG. 9 illustrates, in one example, use of an exemplary impact tool to evaluation the natural frequencies of the surgical robot of FIG. 1, in accordance with one or more aspects of the present disclosure.

With reference to FIGS. 9 and 10, the robot 10 may be configured to prevent the generation of vibrations and/or limit the amplitude of vibratory forces/motions by avoiding frequencies of operation of the end effector 14 that are at or near the natural frequency of the robot 10 or aspects thereof (or that cause frequencies in the robot 10 that are or near the natural frequency of the robot 10 or aspects thereof). In this way, the robot 10 may be configured such that the end effector 14 operates at frequencies that are greater or less than the natural frequency of the robot 10, such as at least by 3% thereof, at least by 5% thereof, at least by 7% thereof or at least by 10% thereof. In some embodiments, the end effector 14 may be configured to operate such that the components of the end effector 14, such as the attachment arm 30, and/or the cutting tool 16 are operated at oscillation frequencies that are greater or less than the natural frequency of the robot 10 (such as at least by 3% thereof, at least by 5% thereof, at least by 7% thereof or at least by 10% thereof).

As is known in the art, the robot 10 comprises a natural frequency at which it will tend to oscillate in the absence of any driving or damping force. When a periodic force is applied is applied to the robot 10, such as from the driving portion 37 of the end effector 14 (e.g., a motor), the amplitude of vibrations will increase drastically if the periodicity is at or close to the natural frequency of the system. This natural phenomenon is known as resonance.

In some embodiments, the natural frequency or resonance of the robot 10 may be evaluated so that generation of such frequencies by the end effector 14 is avoided during a cutting operation via the cutting tool 16. For example, as shown in FIG. 9, in some embodiments, forces may be applied to the end effector 14 (or the cutting tool 16 or articulated arm 12, for example) over a range of frequencies (e.g., via an impact hammer or other device) via a periodic hammer device or related or like device or system 55. In some such embodiments, the periodic forces/motions may be applied along the axial/longitudinal direction (e.g., an X direction/orientation on the cartesian coordinate system), along the lateral direction (perpendicular to the axial/longitudinal direction along the plane of the blade 16 and/or the cutting pathway 17 and/or the motion pathway 15) (e.g., a Y direction/orientation on the cartesian coordinate system), and/or a vertical or height direction that is orthogonal to the longitudinal and lateral directions (e.g., a Z direction on the cartesian coordinate system). During such an application of periodic forces/motions, the positional or spatial movement of the robotic device 1 (e.g., the end effector 14 and/or the cutting blade 16) can be monitored, such as via one or more position sensor or other device. The natural frequency zone of frequencies, and other frequencies which produce vibrations of relatively large amplitudes, can thereby be determined. For example, in some embodiments, the natural frequency zone of frequencies, and other frequencies which produce vibrations of relatively large amplitudes, are thereby determined for the X, Y and Z directions at the end effector 14 and/or cutting blade 16, as shown in FIG. 9.

In order to configure the end effector 14 of the robot 14 in consideration of the natural frequencies of the robot 10 (e.g., via periodic forces/motions applied at or near the end effector 14, for example) to mitigate the amplitude of the vibratory forces/motions generated during a cutting operation (i.e., during operation of the drive portion 37 of the end effector 14), the drive portion 37 of the end effector 14 may be configured such that it operates within a potential operating frequency range at a frequency that substantially differs from the determined natural frequencies, as shown in FIG. 10. The potential operating frequency range is the frequencies of the drive portion 37 (e.g., a motor) that ultimately effectuate rates of oscillation/frequencies of the cutting tool 16 along the cutting pathway 17 at which the cutting tool 16 is configured to suitably/properly/appropriately cut a desired material (e.g., bone). For example, in some embodiments, the end effector 14 may be configured or tuned such that the drive portion 37 operates at a frequency that is within a potential operating frequency range but is greater than or less than the determined resonant frequencies (as described above), or otherwise corresponds to frequencies (e.g., in the X, Y and Z directions) which produced relatively minimal vibration amplitudes during the natural frequency determinations. In some embodiments, the drive portion 37 of the end effector 14 may be operated (e.g., at a frequency) such that the components of the robot 10 that are oscillated by the drive portion 37, such as the attachment mechanism 40 and/or the cutting blade 16), oscillate at a frequency (e.g., in the X, Y and Z directions) that is within a potential operating frequency range but is greater than or less than the determined resonant frequencies (as described above), or otherwise corresponds to frequencies which produced relatively minimal vibration amplitudes during the natural frequency determinations.

As also shown in FIG. 10, in some embodiment, the robot 10 may be configured to minimize the generation of deleterious vibrations from the forces/motions applied by the drive portion 37 of the end effector 14 by tuning the mass of the robot 10 to shift the natural frequency thereof such that it does not fall within or substantially near a desired operating frequency range. For example, after determining a natural frequency or other frequencies that similarly produce elevated vibrations (e.g., elevated amplitudes) through the robot 10 via a periodic force applied at/by the end effector 14, a desired operating frequency or frequency range of the drive portion 37 (or that is effectuated by the drive portion 37) can be compared thereto to determine if there is overlap. If there is overlap, in some embodiments, weight (i.e., mass) may be added to the robot 10, such as to the end effector 14 and/or the cutting tool 16, to lower the natural and deleterious frequencies (i.e., those with relatively high amplitudes) and, thereby, lower the frequencies of the natural and deleterious frequencies such that they fall outside of the desired operating range of the drive portions 37 (i.e., the periodically applied force of the end effector 14). Similarly, in some other embodiments as shown in FIG. 10, if there is overlap between the natural and deleterious frequencies and the desired operating range, weight (i.e., mass) may be removed from the robot 10, such as from the end effector 14 and/or the cutting tool 16, to increase the natural and deleterious frequencies (i.e., those with relatively high amplitudes) and, thereby, lower the frequencies of the natural and deleterious frequencies such that they fall outside the desired operating range of the drive portions 37 (i.e., the periodically applied force of the end effector 14).

As shown in FIGS. 1, 2 and 11-16, the end effector 14 may be coupled to the end (or distal or last) arm segment 18 of the articulated arm 12 via a flange connector assembly 19. For example, at least a portion of the flange connector assembly 19 may be positioned between the distal end portion of the end arm segment 18 and a side portion (e.g., a top or lateral side portion) of the end effector 14. The flange connector assembly 19 may also be referred to as, for example, a mounting flange connector assembly, surgical robot arm flange connector assembly, or output flange connector assembly or simply connector assembly.

The flange connector assembly 19 is configured to couple a rotation adjustment portion 70 of the end arm segment 18 and the end effector 14. For example, the rotation adjustment portion 70 may rotatably couple the end arm segment 18 and the end effector 14 such that the end effector 14 is adjustably rotatably coupled with the end arm segment 18 and the end effector 14 rotates about the longitudinal axis X2-X2. The rotation adjustment portion 70 may thereby be a motorized joint or the like that selectively rotates the end effector 14, and thereby the cutting tool 16, about the longitudinal axis X2-X2. In some embodiments, the adjustment portion 70 may be powered (e.g., include a motor or other movement mechanism) such that it effectuates or adjusts the orientation of the effector 14 with respect to the end arm segment 18, such as about the longitudinal axis X2-X2 thereof. In some embodiments, the adjustment portion 70 may be fixedly (i.e., non-rotatably) coupled to the end arm segment 18 and/or the end effector 14. In some other embodiments, the adjustment portion 70 may be rotatably coupled to the end arm segment 18 and/or the end effector 14.

In some embodiments, the end arm segment 18 (e.g., the adjustment portion 70 thereof) may be coupled to the end effector via the flange connector assembly 19, and the flange connector assembly 19 may be configured as a quick connector to selectively quickly and easily manually remove the end effector 14 from the end arm segment 18. In some such embodiments, the flange connector assembly 19 may be configured as two connector assemblies, such as first and second quick connectors. As shown in FIGS. 11-16, the flange connector assembly 19 may include a first connection assembly 72 (e.g., a first quick connector assembly) that selectively/removably fixedly couples the end segment 18 and a first side of the flange member or plate 76, and a second connection assembly 74 (e.g., a first quick connector assembly) that selectively/removably fixedly couples a second side of the flange member or plate 76 and the end effector 14.

In some embodiments, the first connection assembly 72 may include a first female connector 73A fixed to the end of the end arm segment 18 (e.g., the adjustment portion 70) and a first male connector 73B fixed to a side of the flange member or plate 76, as shown in FIGS. 11-16. The first female and male connectors 73A, 73B are configured to removably manually fixedly mate and coupled together with the first male connector 73B positioned within a cavity or opening of the first female connector 73A. For example, in some embodiments, the cavity or opening of the first female connector 73A may include a first wall or bar portion with a gap there behind, and at least one second wall portion with a gap there behind that is spaced about the longitudinal axis X2-X2 from the first wall or bar portion. In some such embodiments, the first male connector 73B may include a first projection that is configured to be seated within the gap behind the first wall or bar portion, and at least one second projection that is configured to be seated within the gap behind the at least one second wall portion when the first male connector 73B is positioned within the first female connector 73A to removably fixedly couple the end segment 18 and the flange member 76, as shown in FIGS. 11-16. The at least one second projection of the first male connector 73B may be manually movably (such as spring biased) between extended and retracted positions to allow for selective positioning of the first male connector 73B within the first female connector 73A (i.e., coupling), and selective removal of the first male connector 73B from the first female connector 73A (i.e., decoupling). The cavity of the first female connector 73A and the first male connector 73B mat include other recesses and mating projections configured to clock or orient them and/or prevent relative rotation there between about the longitudinal axis X2-X2, as shown in FIGS. 11-16.

Figure 13:
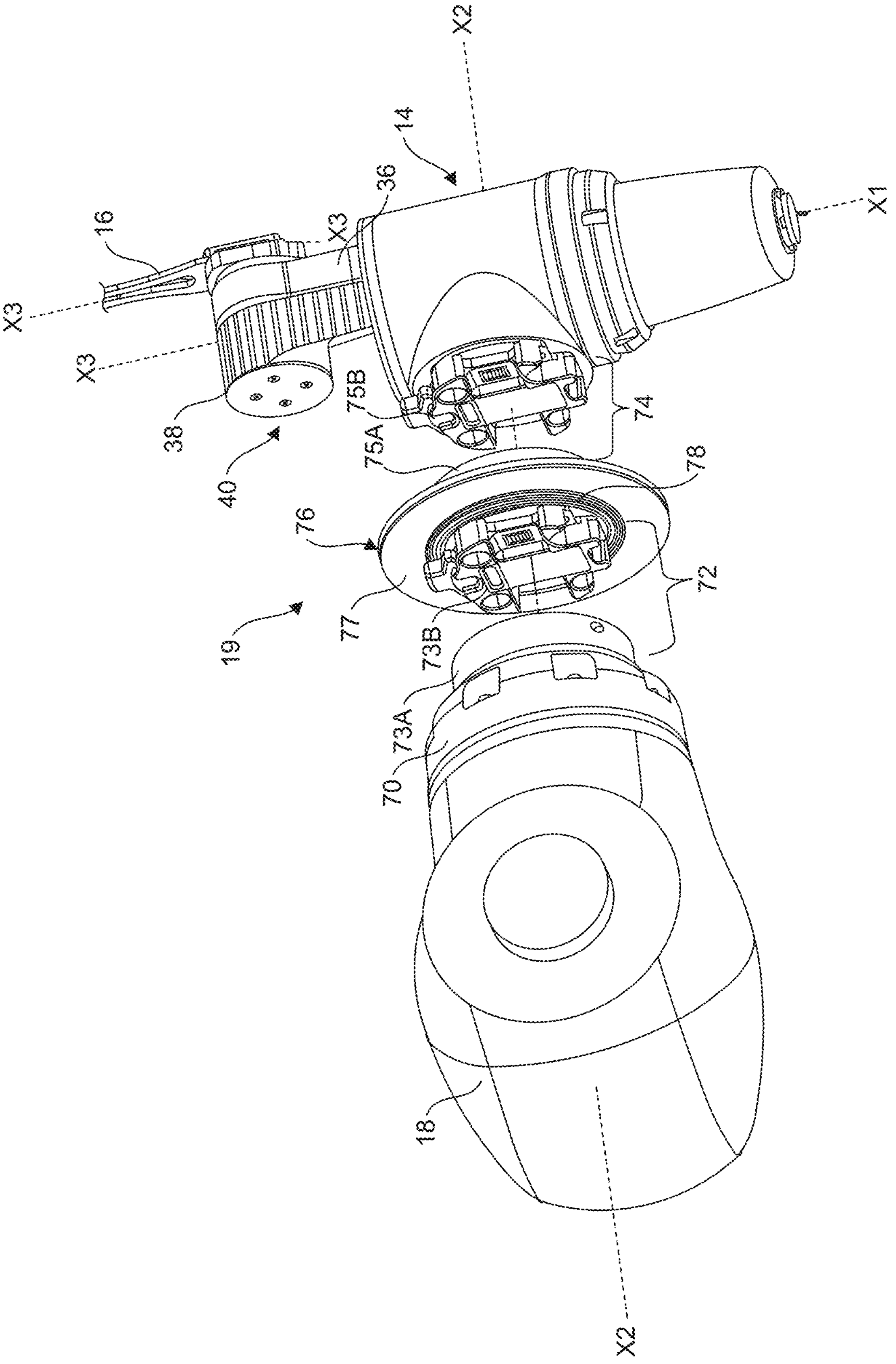
FIG. 13 illustrates, in one example, another exploded perspective view of the end arm segment, connector assembly and end effector of the surgical robot of FIG. 1, in accordance with one or more aspects of the present disclosure.
Figure 14:
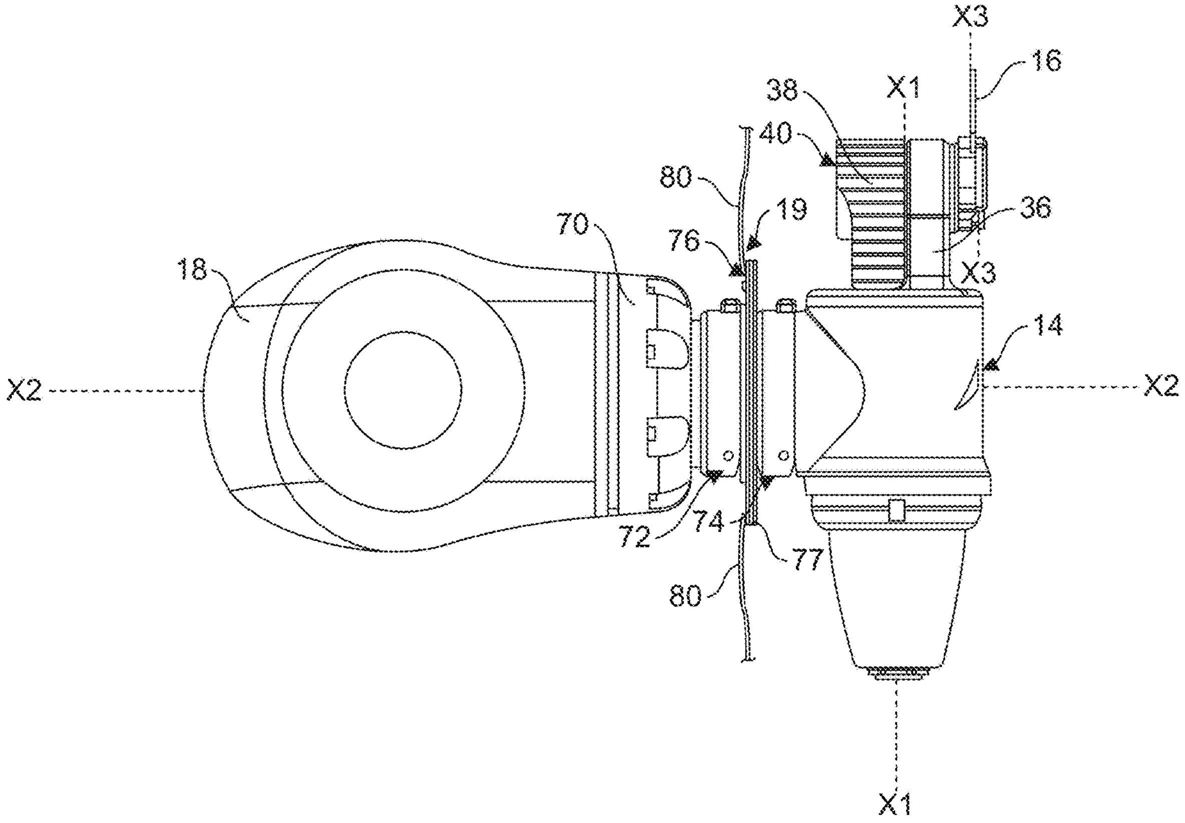
FIG. 14 illustrates, in one example, a side view of the end arm segment, connector assembly and end effector of the surgical robot of FIG. 1, in accordance with one or more aspects of the present disclosure.
Figure 15:
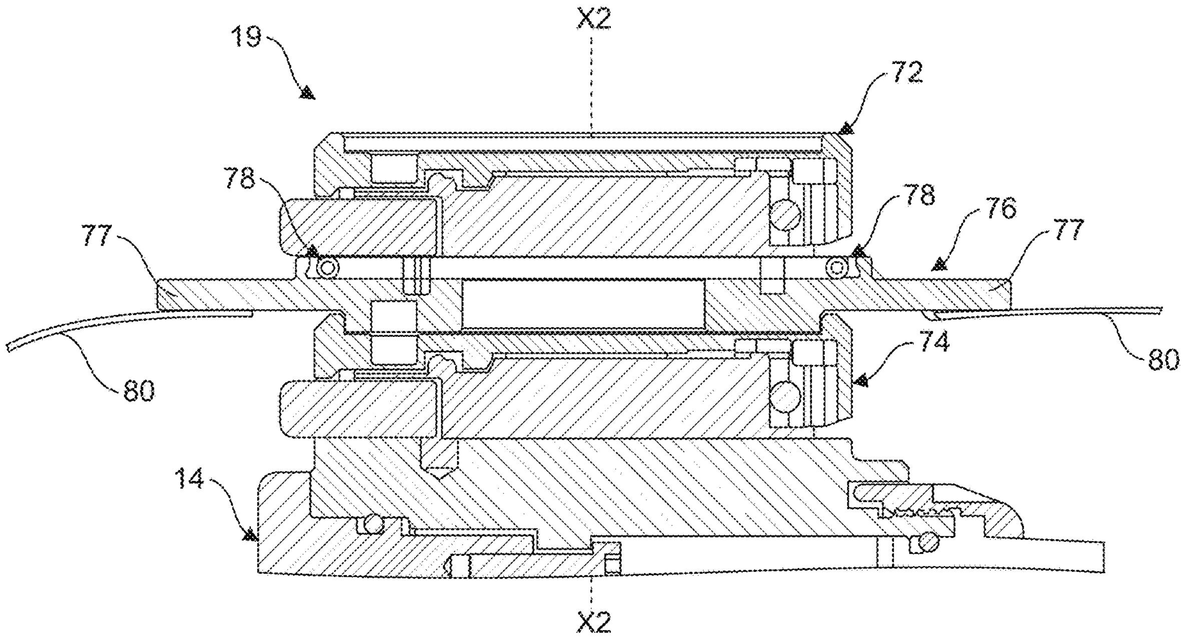
FIG. 15 illustrates, in one example, a side cross-sectional view of the connector assembly and end effector of the surgical robot of FIG. 1, in accordance with one or more aspects of the present disclosure.

To prevent and/or limit the vibratory forces/motions (e.g., minimize the amplitude thereof), that are generated by the end effector 14 and/or a cutting operation from passing to/through the end arm segment 18, the first connection assembly 72 may include a vibration dampening feature. For example, as shown in FIGS. 13 and 15, the flange member 76 may include a coupling recess with a compressible/flexible vibration dampening member 78 positioned therein extending about the first male connector 73B. The coupling recess and vibration dampening member 78 are configured to mate with a rim portion of the first female connector 73A when the first female and male connectors 73A, 73B are coupled together. In some embodiments, the flange connector assembly 19 is configured such that the vibration dampening member 78 is compressed/in compression between the rim portion of the first female connector 73A and the recess of the flange member 76 about the first male connector 73B (in a direction extending along the axis X2-X2) when the first female and male connectors 73A, 73B are coupled together.

The vibration dampening member 78 is configured to dampen the vibratory forces/motions applied thereto via the end effector 14. The vibration dampening member 78 is thereby configured to dissipate the cyclical energy (e.g., vibratory forces/motion) applied thereto by the end effector 14/cutting tool 16. In some embodiments, the vibration dampening member 78 may be configured to provide viscoelastic damping. In some embodiments, the vibration dampening member 78 is made from or comprises an inertia mass and an energy dissipating material, such as rubber (natural or synthetic) (such as, but not limited to, latex, silicone rubber or silicone-free rubber), synthetic elastomer (polyurethane, polyvinyl chloride (PVC), etc.), a spring, a fluid or some combination thereof. By way of a non-limiting example, the vibration dampening member 78 may comprise be an O-ring.

As shown in FIGS. 11-16, in some embodiments, the second connection assembly 74 may be configured substantially similar to the first connection assembly 72 and include a second female connector 75A fixed to other side of the flange member or plate 76 and a second male connector 75B fixed to a side (e.g., top lateral side) of the end effector 14. The second male and female connectors 75B, 75A may be configured substantially the same or similar as the first female and male connectors 73A, 73B, and is not repeated herein for brevity sake. The second male connector 75B may or may not include a groove or recess and a compressible/flexible vibration dampening member 78 (e.g., O-ring) positioned therein for connection to a rim portion of the second female connector 75A.

Figure 16:
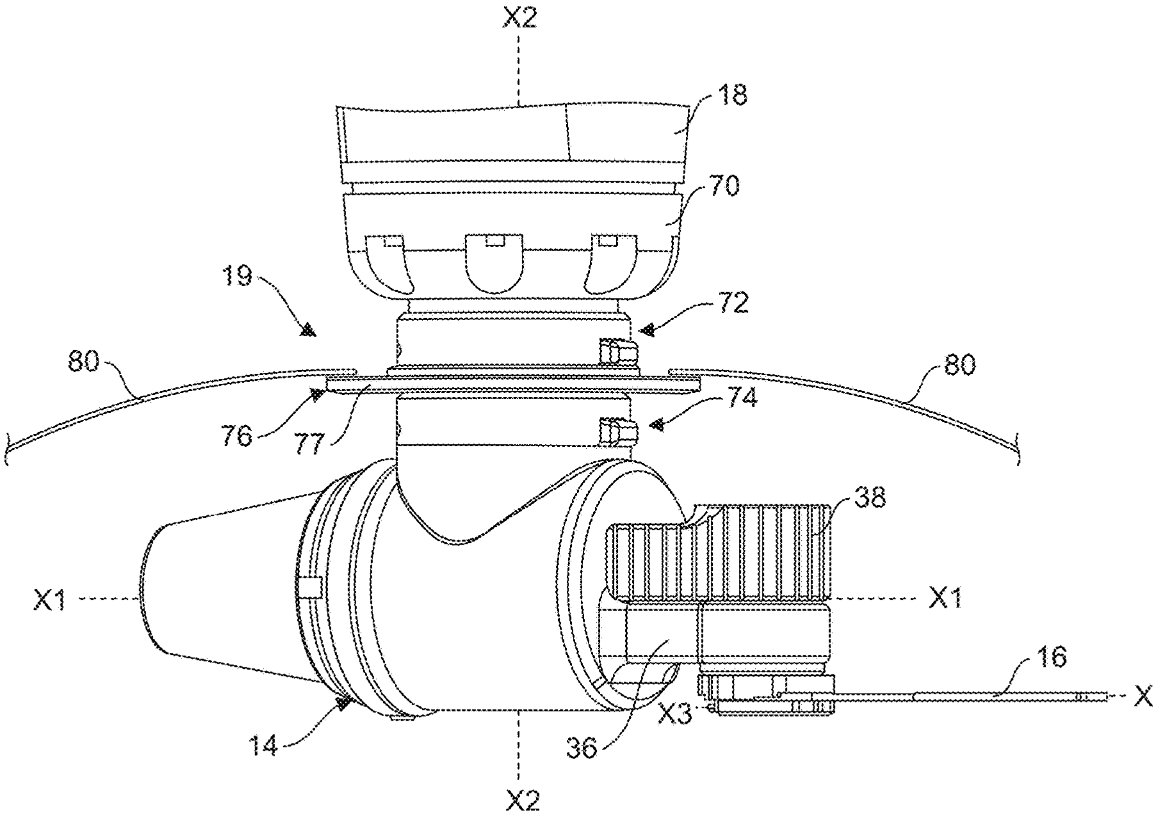
FIG. 16 illustrates, in one example, a side view of the end arm segment, connector assembly and end effector of the surgical robot of FIG. 1, in accordance with one or more aspects of the present disclosure.

As shown in FIGS. 13-16, the flange member 76 of the flange connector assembly 19 may include a sterility portion or ring 77 that extends about the axis X2-X2. As also shown in FIGS. 13-16 a surgical drape, curtain or the like 80 may be coupled to the sterility portion 77 of the sterility portion or ring 77 in a sterile sealed manner. The flange connector assembly 19 and the surgical drape 80 thereby defines a sterility barrier between the end effector 14 and the cutting tool 16 and the arm 12 and base portion of the robot 10. As shown in FIG. 16, a top portion of the end effector 14 that is spaced furthest from the attachment mechanism 40 and cutting tool 16 may be coupled with the second connection assembly 74 so that the surgical drape 80 is spaced from the cutting tool 16.

Figure 17:
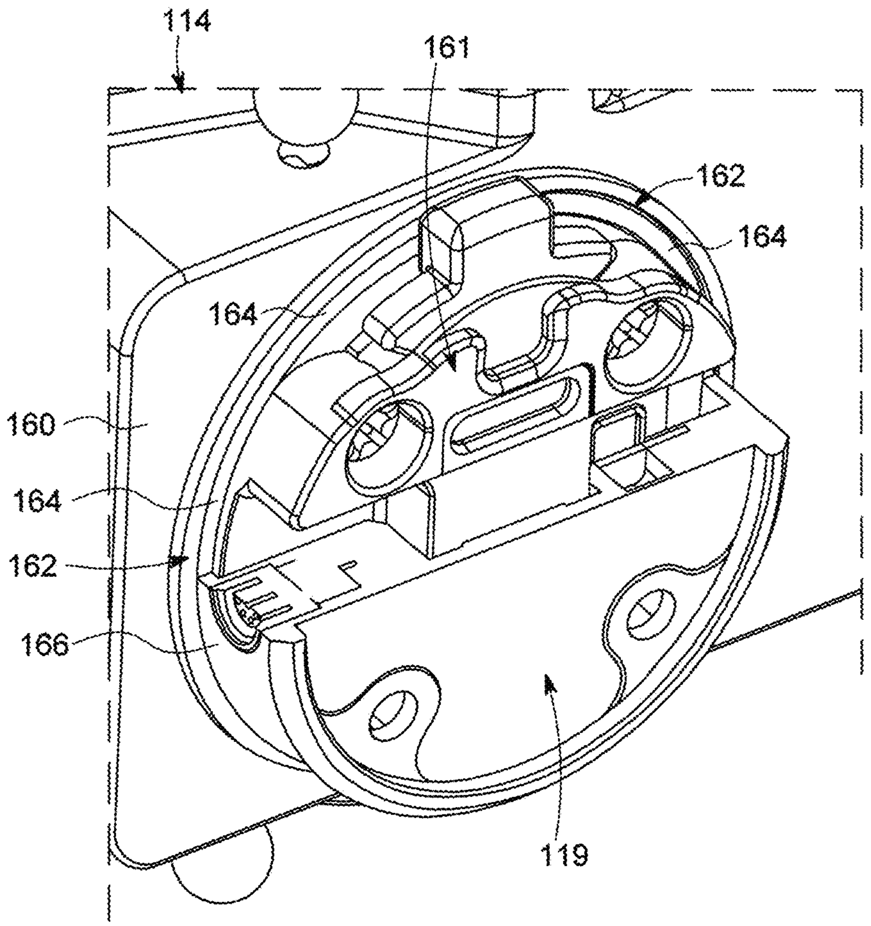
FIG. 17 illustrates, in one example, an elevation perspective partial-cutaway view of a connector assembly coupling n end effector and a distal arm segment of a surgical robot, in accordance with one or more aspects of the present disclosure.
Figure 18:
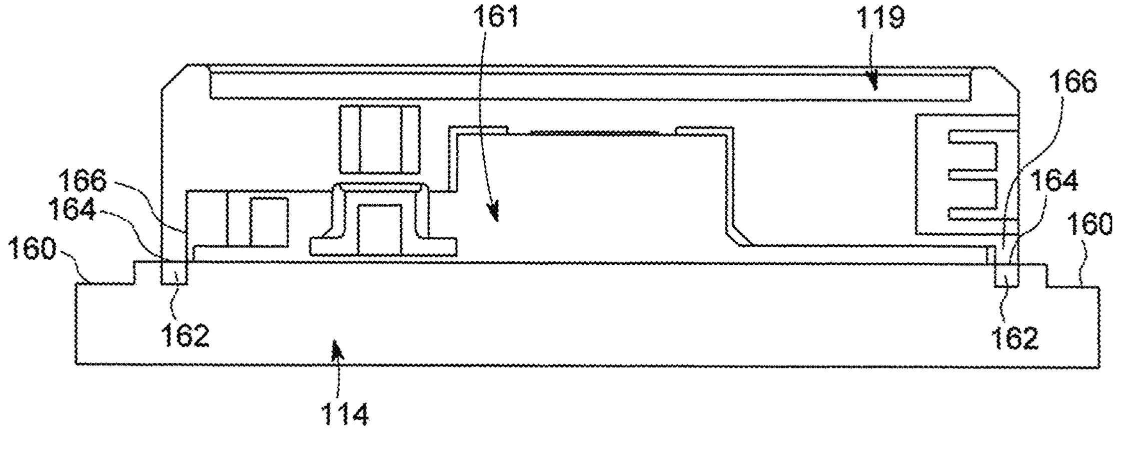
FIG. 18 illustrates, in one example, a cross-sectional side view of the connector assembly of FIG. 17, in accordance with one or more aspects of the present disclosure.

Another exemplary surgical robotic system 110 that is shown in FIGS. 17 and 18 that includes a different connection between the end effector 114 and the end segment 118 of the arm 112 than the flange connector assembly 19 described above. The surgical robot 110 of FIGS. 17 and 18 is substantially similar to the surgical robot 10 described herein, and therefore like reference numerals preceded with "1" are used to indicate like components, aspects, portions, functions, processes and the like, and the description above directed to thereto equally applies, and is not repeated for brevity and clarity purposes.

As shown in in FIGS. 17 and 18, the end effector 114 may include a coupling recess or slot 162 positioned proximate to the connector 161. In some embodiments, the coupling recess 162 may be adjacent to the periphery of the connector 161. As shown in FIGS. 17 and 18, in some embodiments, the coupling recess 162 may extend annularly about at least a portion of the connector 161 (e.g., extend circumferentially thereabout). In one such embodiments, the coupling recess 162 may be circular.

To prevent and/or limit the vibratory forces/motions (e.g., minimize the amplitude thereof), that are generated by the end effector 114, from passing to/through the end arm segment 118, the coupling recess 162 includes a compressible/flexible vibration dampening member 164 positioned therein. The vibration dampening member 64 is configured to dampen the vibratory forces/motions applied thereto by the end effector 114. The vibration dampening member 164 is thereby configured to dissipate the cyclical energy (e.g., vibratory forces/motion) applied thereto by the end effector 14. In some embodiments, the vibration dampening member 164 may be configured to provide viscoelastic damping. In some embodiments, the vibration dampening member 64 is made from or comprises an inertia mass and an energy dissipating material, such as rubber (natural or synthetic) (such as, but not limited to, latex, silicone rubber or silicone-free rubber), synthetic elastomer (polyurethane, polyvinyl chloride (PVC), etc.), a spring, a fluid or some combination thereof. By way of a non-limiting example, the vibration dampening member 164 may comprise be an O-ring.

As shown in in FIGS. 17 and 18, the flange connector assembly 119 includes a projection or rim 166 that is cooperatively configured with respect to the coupling recess 162 such that when the flange connector assembly 119 is coupled with the end effector 114 via the connector 161 (i.e., the flange connector assembly 119 is coupled with connector 161, and the connector 161 is coupled with the end effector 114), the projection 166 is received within the coupling recess 162 with the vibration dampening member 164 positioned at least partially therebetween. In some embodiments, the flange connector assembly 119 is configured such that the vibration dampening member 164 is compressed/in compression between the projection 166 and the coupling recess 162 when the flange connector assembly 119 is coupled with the connector 161 of the end effector 114. In some embodiments, the vibration dampening member 164 is positioned between and compressed in a direction extending along the axis X2-X2 of the end segment 118 and/or substantially perpendicular to the axis X1-X1 of the end effector 114 and cutting blade 116.

The robot 110 may thereby be configured such that the vibration dampening member 64 dampens vibrations between the end effector 114 and the end segment 118, such as vibratory forces/motions generated by the end effector 114 to minimize translation of the vibrations (e.g., amplitude thereof) into the articulated arm 112. Further, the compression of the vibration dampening member 164 between the projection 166 of the flange connector assembly 119 and the coupling recess 162 of the end effector 114 when the flange connector assembly 119 is coupled with the connector 161 of the end effector 114 thereby preloads the vibration dampening member 164. Such preloaded force of the vibration dampening member 164 thereby preloads the connection between the end effector 114 and the connector assembly 19/end segment 118, which further tends to reduce vibrations and/or relative movement therebetween and strengthens the coupling connection.

Figure 19:
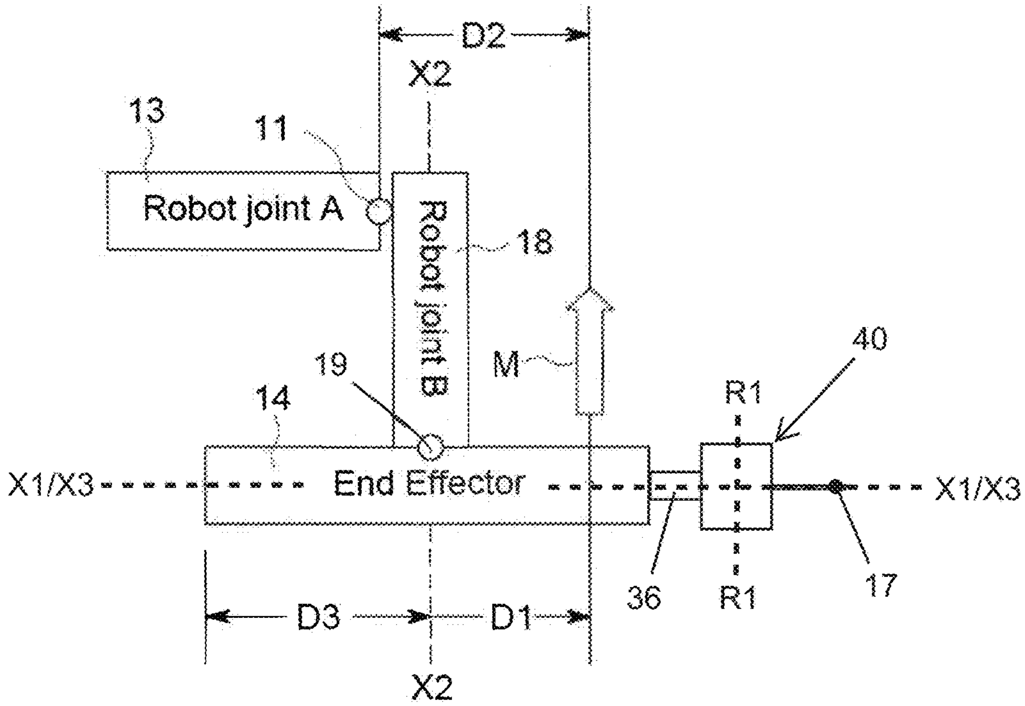
FIG. 19 graphically illustrates, in one example, moment forces due to the arrangement of the end effector and cutting blade with respect to arm segments of the of the surgical robot of FIG. 1, in accordance with one or more aspects of the present disclosure.
Figure 20:
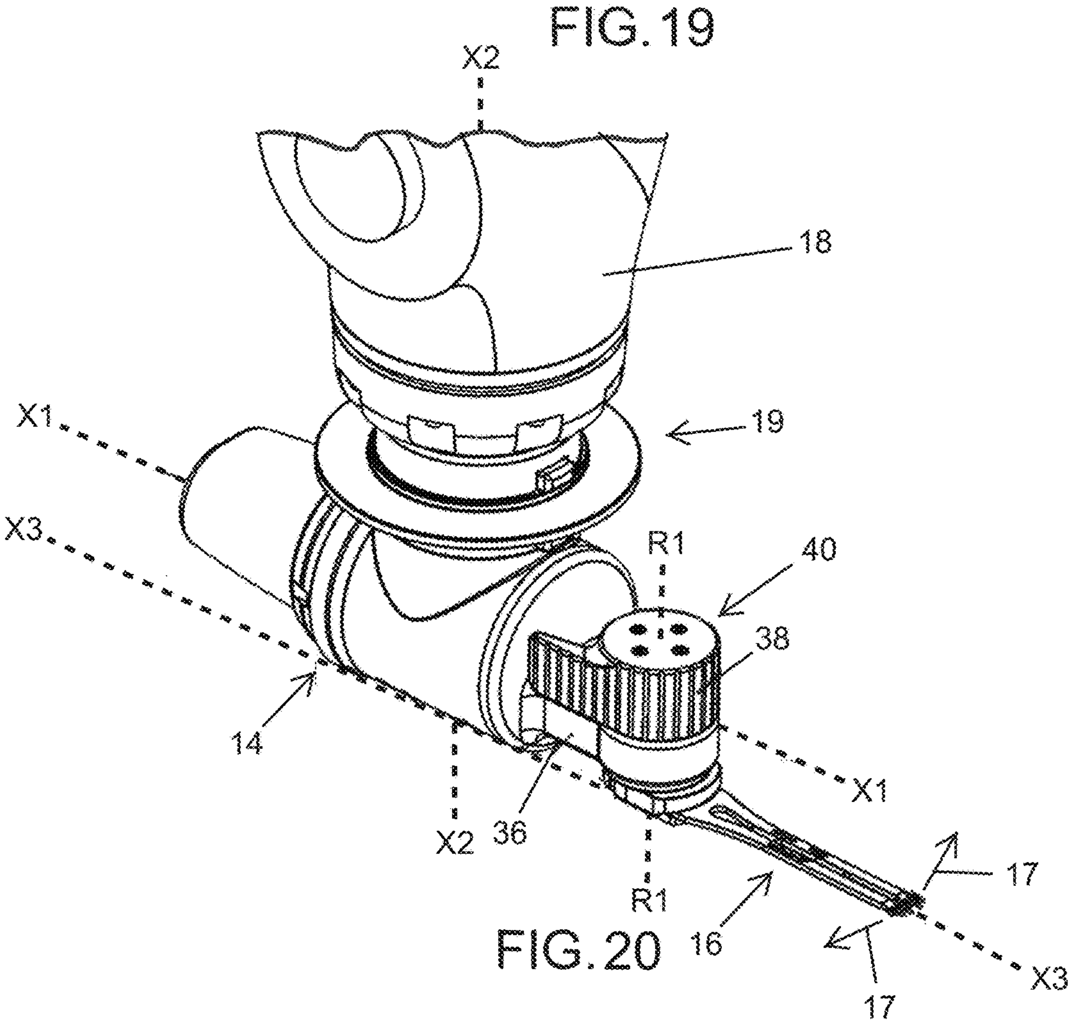
FIG. 20 illustrates, in one example, an elevational perspective view of the end effector and cutting blade and the distal arm segment of the of the surgical robot of FIG. 1, in accordance with one or more aspects of the present disclosure.

As shown in FIGS. 19 and 20, the orientation of end effector 14 and cutting blade 16 with respect to the articulated arm 12 to minimizes the moment forces acting on the arm 12 and to the reduce load on the joints of the arm 12 during a cutting operation. For example, as shown in FIGS. 19 and 20, the end effector 14 may be extended or elongate along the longitudinal or axial direction extending along the axis X1-X1 thereof. Stated differently, the end effector 14 may be configured such that its maximum longitudinal/axial length is greater than its maximum lateral width. Further, as described above and shown in FIGS. 19 and 20, the cutting tool 16 may extend axially from the attachment mechanism 40 at a front longitudinal/axial end portion of the end effector 14. As also explained above and shown in FIGS. 19 and 20, the cutting tool 16 may be a sagittal cutting blade configured to cut when it is oscillated or translated along the cutting pathway 17 which extends along a lateral direction and advanced axially/longitudinally into/through a material to be cut (e.g., bone or other tissue). Thereby, in such embodiments and as depicted in FIG. 19, the forces generated by the end effector 14 (e.g., via the drive portion 37) are angled (e.g., perpendicular) with respect to the axis X2-X2 of the end segment 18 of the articulated arm 12 and axially/longitudinally spaced therefrom such that they act as a torque or moment force M on the joint 19 between the end effector 14 and the end segment.

As shown in FIGS. 19 and 20, the robot 10 is configured with the end segment 18 being coupled to a top lateral side of the end effector 14 spaced from the longitudinal/axial back end thereof. In some embodiments, the end segment 18 may be coupled with a medial portion of the top lateral side of the end effector 14 along its longitudinal/axial length. The distance D1 between the axis X2-X2 of the end segment 18 (which may pass through the center of the coupling joint 19), and the force applied by the drive portion 37 of the end effector 14, is thereby minimized so as to minimize the moment of force M acting on the joint 19 and/or end segment 18. It is noted that if, alternatively, the lateral back end of the end effector 14 was coupled to the distal end of the end segment 18, the additional longitudinal/axial length of the end portion of the end effector 14 would increase the moment of force MI by a distance D3 (i.e., the moment of force would be D1+D3), as shown in FIG. 19.

Further, in an alternative arrangement with the axes X1-X1 of the end effector 14 being parallel or aligned with axis X2-X2 of the end segment 18, the flange connector assembly 19 would be configured to rotate the end effector 14 in line with the axis X2-X2 of the end segment 18, as opposed to orthogonal to or about the axis X2-X2 of the end segment 18 as in the arrangement shown in FIG. 19. In some embodiments, the robot 10 may be positioned adjacent to the material or patient that is to be cut (e.g., operated on), as shown in FIG. 1. In such embodiments and with the arrangement shown in FIGS. 19 and 20, in order to perform a cut via the cutting tool 16 that extends downwardly, the end segment 18 can be extended laterally over the material or patient, and the end effector 14 and cutting tool 16 can be rotated about the axis X2-X2 of the end segment 18 to orient the cutting tool 16 for such a cut. It is noted that in the alternative arrangement discussed above with the axis X1-X1 of the end effector 14 being parallel or aligned with axis X2-X2 of the end segment 18, the end segment 18 would have to be oriented downwardly and the adjacent second arm segment 13 connected to the end arm segment 18 would have to be orientated laterally over the material or patient to orient the cutting tool 16 for such a cut. In such a configuration, the articular arm 12 would have a limited ability to spatially move and orient (or options for orienting) the cutting tool 16 as opposed to the arrangement shown in FIGS. 1, 19 and 20, and the orientation is less desirable for vibration mitigation purposes.

The arrangement of the end effector 14 and end arm segment 18 being orthogonal and coupled to the lateral side of the end effector 14 as shown in FIG. 19, the longitudinal/axial distance between the joint 11 connecting the end arm segment 12 and a secondary arm segment 13 of the articulated arm 12 that extends from the end segment 18 is positioned only slightly past the axis X2-X2 of the end arm segment 18. Thereby, the end effector 14 and end arm segment 18 configuration is effective in positioning the force(s) applied by the drive portion 37 of the end effector 14 a minimal longitudinal/axial distance D2 from the joint 11. Again, it is noted that in the alternative arrangement discussed above with the axes X1-X1 of the end effector 14 being parallel or aligned with axis X2-X2 of the end segment 18, the moment of force(s) applied by the end effector 14 to the joint 11 would be increased by the distance D3 (i.e., the moment of force would be D2+D3).

The orthogonal arrangement of the axis X1-X1 of the end effector 14 and the cutting tool 16 also minimizes rotational forces F2 (i.e., twisting) acting on the joints of the articulated arm 12, as shown in FIG. 10. With reference to FIG. 20, in the configuration of robot 10, the forces applied by the end effector 14 (i.e., drive portion 37) acting in the cutting pathway 17 (i.e., oscillation direction or plane) are oriented perpendicular to the axis X2-X2 of the end segment 18 between the end effector 14 and the end arm segment 18, thereby about the joint 19. In some embodiments, the end effector 14 may be mounted on the end segment 17 such that the axis X2-X2 of the end segment 18 (and the joint 19 therebetween) passes through or in substantially proximity to the center of mass of the end effector 14 to further reduce the load of the forces that pass to the joints of the articulated arm 12. It is noted that in alternative embodiment shown in FIG. 3, the forces applied by the end effector 14 (i.e., drive portion 37) acting in the cutting pathway 17 (i.e., oscillation direction or plane) are oriented generally parallel to the axis X2-X2 of the end segment 18, and thus on the joint 19.

It is to be understood that the above description is intended to be illustrative, and not restrictive. For example, the above-described exemplary embodiments, and/or aspects thereof, may be used in combination with each other. In addition, many modifications may be made to adapt a particular configuration according to the teachings of the various examples without departing from their scope. For example, it is expressly disclosed that the cutting tool 16 may not be configured as a sagittal saw blade, but rather a differing type of saw blade. For example, the cutting tool 16 may be configured as a reciprocating type saw blade with cutting teeth (and/or abrasives) arranged along an axially-extending lateral side of blade, or a rotary cutting blade. As another example, the cutting tool 16 may be configured as any other blade-type cutting tool that utilizes an attachment portion 20 to couple with an attachment mechanism 12 of the end effector 14. Still further, the cutting tool 16 may be a non-planar cutting tool, such as a rotary cutting bit or blade, that is rotated by the end effector 14 and is configured to cut via such rotational forces. As such, the configurations of the articulated arm 12, end effector 14 (including the attachment mechanism 40 thereof) and/or the cutting tool 16 described above to prevent the generation, and/or mitigate the effect, of vibrations may be adapted or modified according to the particular configuration of the oscillatory cutting pathway 17 of a particular cutting tool 16, which fall within the scope of this disclosure.

Many other examples will be apparent to those of skill in the art upon reviewing the above description. The scope of the various examples should, therefore, be determined with reference to the appended claims, along with the full scope of equivalents to which such claims are entitled.

While dimensions and types of materials may be described herein, they are intended to define parameters of some of the various examples, and they are by no means limiting to all examples and are merely exemplary.

In the appended claims, the terms "including" and "in which" are used as the plain-English equivalents of the respective terms "comprising" and "wherein." Moreover, in the following claims, the terms "first," "second," and "third," etc. are used merely as referee labels, and are not intended to impose numerical, structural or other requirements on their objects. Forms of term "based on" herein encompass relationships where an element is partially based on as well as relationships where an element is entirely based on. Forms of the term "defined" encompass relationships where an element is partially defined as well as relationships where an element is entirely defined. Further, the limitations of the following claims are not written in means-plus-function format and are not intended to be interpreted based on 35 U.S.C. § 112, sixth paragraph, unless and until such claim limitations expressly use the phrase "means for" followed by a statement of function cavity of further structure. It is to be understood that not necessarily all such objects or advantages described above may be achieved in accordance with any particular example. Thus, for example, those skilled in the art will recognize that the devices, systems and methods described herein may be embodied or carried out in a manner that achieves or optimizes one advantage or group of advantages as taught herein without necessarily achieving other objects or advantages as may be taught or suggested herein.

While the disclosure has been described in detail in connection with only a limited number of examples, it should be readily understood that the disclosure is not limited to such disclosed examples. Rather, this disclosure can be modified to incorporate any number of variations, alterations, substitutions or equivalent arrangements not heretofore described, but which are commensurate with the spirit and scope of the disclosure. Additionally, while various examples have been described, it is to be understood that aspects of the disclosure may include only one example or some of the described examples. Also, while some disclosure are described as having a certain number of elements, it will be understood that the examples can be practiced with less than or greater than the certain number of elements.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein.

We claim:

1. A robotic system comprising:

an articulated arm comprising a plurality of arm segments defining longitudinal axes, and adjustable joints coupled between adjacent arm segments that are configured to adjust an orientation of the axes of the adjacent arm segments; and an end effector rotatably coupled to an end arm segment of the plurality of arm segments comprising a powered drive portion, wherein the end effector comprises a cutting tool attachment mechanism positioned at a longitudinal end of the end effector that is configured to couple with the cutting tool such that the cutting tool extends axially therefrom, and the powered drive portion translates the cutting tool along a cutting pathway along which the cutting tool is configured to effectuate cutting that is angled with respect to a longitudinal axis of the cutting tool, and wherein the end effector is oriented such that the longitudinal axis of the cutting tool is angled with respect to the axis of the end arm segment, wherein the end effector is coupled to the end arm segment via a manually operable connector assembly, the connector assembly comprising a flange assembly with a first connector removably coupling the end arm segment and a flange member of the flange assembly, and a second connector removably coupling the flange member and the end effector, and wherein the connector assembly further comprises a surgical drape extending from the flange member about the flange member.

2. The robotic system of claim 1, wherein the cutting tool is configured to cut when oscillated along the cutting pathway about an axis of oscillation.

3. The robotic system of claim 1, wherein the end effector is oriented such that the longitudinal axis of the cutting tool is oriented substantially perpendicular with respect to the axis of the end arm segment.

4. The robotic system of claim 1, wherein the end effector defines a second longitudinal axis, and wherein the end effector is oriented such that the second longitudinal axis is angled with respect to the axis of the end arm segment.

5. The robotic system of claim 4, wherein the second longitudinal axis is oriented substantially perpendicular with respect to the axis of the end arm segment.

6. The robotic system of claim 1, wherein the end effector is longitudinally elongated such that is defines a maximum longitudinal length that is greater than a maximum lateral width.

7. The robotic system of claim 6, wherein the end arm segment is rotatably coupled with a lateral side portion of the end effector that is longitudinally spaced from a longitudinal end of the end effector that opposes the attachment mechanism.

8. The robotic system of claim 1, wherein the cutting tool is configured as a sagittal cutting tool with cutting teeth positioned at the longitudinal end thereof, the sagittal cutting tool being configured to cut when oscillated along the cutting pathway about the axis of oscillation and translated longitudinally.

9. The robotic system of claim 1, wherein the cutting tool is configured such that it comprises a center of mass that is substantially aligned with the axis of oscillation.

10. The robotic system of claim 9, wherein the cutting tool is configured such that the axis of oscillation is substantially aligned with the longitudinal axis thereof.

11. The robotic system of claim 1, wherein the attachment mechanism comprises an attachment arm with a first portion that is coupled with the powered drive portion and extends longitudinally therefrom, wherein the attachment arm is oscillated by the powered drive portion about a second axis of oscillation, and wherein the attachment arm is configured to transfer said oscillation to the cutting tool to oscillate the cutting tool.

12. The robotic system of claim 11, wherein the attachment arm is configured such that the second axis of oscillation is substantially aligned with a longitudinal axis thereof.

13. The robotic system of claim 11, wherein the attachment arm is configured such that it comprises a center of mass that is substantially aligned with the second axis of oscillation.

14. The robotic system of claim 11, wherein the first and second axes of oscillation are parallel.

15. The robotic system of claim 1, wherein the cutting tool comprises a cutting tool with a body portion that comprises plurality of longitudinally spaced apertures to minimize a total mass of the cutting tool.

16. The robotic system of claim 1, wherein the attachment arm comprises a body portion that comprises at least one aperture configured to minimize a total mass of the attachment arm.

17. The robotic system of claim 1, wherein the powered drive portion of the end effector is configured to apply an oscillatory force at a frequency that is greater than or less than a resonant frequency range of the robotic system and that oscillates the cutting tool along the cutting pathway in a cutting operation frequency range of the cutting tool.

18. The robotic system of claim 1, wherein the powered drive portion of the end effector is configured to apply an oscillatory force at a frequency that is greater than or less than a resonant frequency range of the robotic system and that oscillates the cutting tool along the cutting pathway in a cutting operation frequency range of the cutting tool, wherein the cutting pathway is a planar arc defined by radius extending from an axis of rotation, and wherein the end effector is coupled to the end arm segment via a manually operable connector assembly comprising a flange assembly with a first connector removably coupling the end arm segment and a flange member of the flange assembly, a second connector removably coupling the flange member and the end effector, and a flexible vibration dampening member positioned within mating components of at least one of the first connector and the second connector.

19. The robotic system of claim 1, wherein the end effector is coupled to the end arm segment such that the end effector is rotatable about the axis of the end arm segment.

20. The robotic system of claim 1, wherein the end effector is coupled to the end arm segment such that the end effector is only rotatable about the axis of the end arm segment.

21. The robotic system of claim 1, wherein the end effector is coupled to the end arm segment via a rotatable joint.

22. The robotic system of claim 1, wherein the connector assembly further comprises a flexible vibration dampening member positioned within mating components of at least one of the first connector and the second connector.

23. The robotic system according to claim 1, wherein the cutting tool comprises a cutting blade.

24. The robotic system according to claim 1, wherein the robotic system is configured as an autonomous robot that autonomously translates the cutting tool through one or more cutting pathways without a user physically engaging the robotic system.

25. The robotic system according to claim 1, wherein the cutting pathway is planar.

26. The robotic system according to claim 25, wherein the cutting pathway is oriented substantially perpendicular with respect to the axis of the end arm segment.

27. The robotic system according to claim 25, wherein the cutting pathway is an arc defined by radius extending from an axis of rotation.

28. The robotic system according to claim 27, wherein the axis of rotation is oriented substantially parallel with respect to the axis of the end arm segment.

29. A robotic system comprising:

an articulated arm comprising a plurality of arm segments defining longitudinal axes, and adjustable joints coupled between adjacent arm segments that are configured to adjust an orientation of the axes of the adjacent arm segments; and an end effector rotatably coupled to an end arm segment of the plurality of arm segments comprising a powered drive portion, wherein the end effector comprises a cutting tool attachment mechanism positioned at a longitudinal end of the end effector that is configured to couple with the cutting tool such that the cutting tool extends axially therefrom, and the powered drive portion translates the cutting tool along a cutting pathway along which the cutting tool is configured to effectuate cutting that is angled with respect to a longitudinal axis of the cutting tool, and wherein the end effector is oriented such that the longitudinal axis of the cutting tool is angled with respect to the axis of the end arm segment, wherein the end effector is coupled to the end arm segment via a manually operable connector assembly, the connector assembly comprising a flange assembly with a first connector removably coupling the end arm segment and a flange member of the flange assembly, and a second connector removably coupling the flange member and the end effector, wherein the connector assembly further comprises a flexible vibration dampening member positioned within mating components of at least one of the first connector and the second connector, and wherein the flexible vibration dampening member is positioned within a recess of the flange member and engages a portion of the first connector coupled to the end arm segment.

30. The robotic system of claim 29, wherein the vibration dampening member is under a compressive preload between the recess and the portion of the first connector.

31. A robotic system comprising:

an articulated arm comprising a plurality of arm segments defining longitudinal axes, and adjustable joints coupled between adjacent arm segments that are configured to adjust an orientation of the axes of the adjacent arm segments; and an end effector rotatably coupled to an end arm segment of the plurality of arm segments comprising a powered drive portion, wherein the end effector comprises a cutting tool attachment mechanism positioned at a longitudinal end of the end effector that is configured to couple with the cutting tool such that the cutting tool extends axially therefrom, and the powered drive portion translates the cutting tool along a cutting pathway along which the cutting tool is configured to effectuate cutting that is angled with respect to a longitudinal axis of the cutting tool, and wherein the end effector is oriented such that the longitudinal axis of the cutting tool is angled with respect to the axis of the end arm segment, wherein the end effector is coupled to the end arm segment via a manually operable connector assembly, the connector assembly comprising a flange assembly with a first connector removably coupling the end arm segment and a flange member of the flange assembly, and a second connector removably coupling the flange member and the end effector, wherein the connector assembly comprises a first connector that couples the end segment and a first side of the flange member, and a second connector that couples a second side of the flange member and the end effector, and wherein the first connector is a first quick connector, and the second connector is a second quick connector.

32. The robotic system of claim 31, wherein the connector assembly further comprises a surgical drape extending from the flange member about the flange member.

33. The robotic system of claim 31, wherein the first connector comprises a first male connector portion fixed to a first side of the flange member and a first female connector portion fixed to the end arm segment, the first male and female connector portions configured to removably manually couple together, and wherein the second connector comprises a second male connector portion fixed to the end effector and a second female connector portion fixed to the second of the flange member, the second male and female connector portions configured to removably manually couple together.

34. A method of cutting a material, comprising:

utilizing the robotic system according to claim 1 to translate the cutting tool along the cutting pathway and one or more longitudinal pathways to cut the material.

35. The method of claim 34, wherein the material comprises a bone of a mammalian patient, and wherein the cutting tool comprises a sagittal cutting blade.

* * * * *